United States Patent
Grenard et al.

(10) Patent No.: US 7,906,156 B2
(45) Date of Patent: Mar. 15, 2011

(54) CB2 RECEPTORS BLOCKS ACCUMULATION OF HUMAN HEPATIC MYOFIBROBLASTS: A NOVEL ANTIFIBROGENIC PATHWAY IN THE LIVER

(75) Inventors: Pascale Grenard, Bretigny (FR); Boris Julien, Paris (FR); Jeanne Tran Van Nhieu, St. Maur des Fosses (FR); Ariane Mallat, Paris (FR); Sophie Lotersztajn, Paris (FR)

(73) Assignee: Institut National de la Sante et de la Recherche Medicale, Paris Cedex (FR)

( * ) Notice: Subject to any disclaimer, the term of this patent is extended or adjusted under 35 U.S.C. 154(b) by 0 days.

(21) Appl. No.: 12/393,927

(22) Filed: Feb. 26, 2009

(65) Prior Publication Data

US 2009/0221692 A1    Sep. 3, 2009

Related U.S. Application Data

(62) Division of application No. 11/934,470, filed on Nov. 2, 2007, now abandoned, which is a division of application No. 10/956,731, filed on Oct. 1, 2004, now Pat. No. 7,320,805.

(60) Provisional application No. 60/508,178, filed on Oct. 1, 2003.

(51) Int. Cl.
*A61K 36/00* (2006.01)
(52) U.S. Cl. ........................................................ 424/725
(58) Field of Classification Search .................... None
See application file for complete search history.

(56) References Cited

OTHER PUBLICATIONS

Lotersztajn et al. (FASEB Journal (Mar. 2003), vol. 17, No. 4-5, abstract No. 162.7).*

* cited by examiner

*Primary Examiner* — Susan C Hoffman
(74) *Attorney, Agent, or Firm* — Kilpatrick Townsend & Stockton LLP

(57) ABSTRACT

Methods for treating diseases of the livers mediated by CB2 receptors are described. The methods may include administering an effective amount of a cannabinoid, an agent that activates a CB2 receptor, a composition that includes a non-selective agonist of CB2 and a selective antagonist of CB1, a composition that includes an agonist of CB2 receptors, and/or a composition that includes an up-regulator of CB2 receptors to a patient who has liver fibrosis.

5 Claims, 6 Drawing Sheets

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:G
      protein-coupled receptor cannabinoid receptor 2
      (CB2) blocking peptide, residues 20-33 of human
      CB2 receptor

<400> SEQUENCE: 1

Asn Pro Met Lys Asp Tyr Met Ile Leu Ser Gly Pro Gln Lys
1               5                   10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:synthetic
      oligo (dT)-12-18 primer
<220> FEATURE:
<221> NAME/KEY: modified_base
<222> LOCATION: (13)..(18)
<223> OTHER INFORMATION: t at positions 13-18 may be present or absent
```

```
<400> SEQUENCE: 2
tttttttttt tttttttt                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:synthetic
      CB2 oligonucleotide sense primer

<400> SEQUENCE: 3
tttcccactg atccccaatg                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:synthetic
      CB2 oligonucleotide antisense primer

<400> SEQUENCE: 4
agttgatgag gcacagcatg                                                20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:synthetic
      CB2 oligonucleotide probe

<400> SEQUENCE: 5
gaccctaggg ctagtgttgg ctg                                            23
```

CB2 RECEPTORS BLOCKS ACCUMULATION OF HUMAN HEPATIC MYOFIBROBLASTS: A NOVEL ANTIFIBROGENIC PATHWAY IN THE LIVER

CROSS-REFERENCES TO RELATED APPLICATIONS

This application is a divisional of prior U.S. patent application Ser. No. 11/934,470, entitled "CB2 RECEPTORS BLOCKS ACCUMULATION OF HUMAN HEPATIC MYOFIBROBLASTS: A NOVEL ANTIFIBROGENIC PATHWAY IN THE LIVER," filed Nov. 2, 2007 (now abandoned), which is a divisional of U.S. patent application Ser. No. 10/956,731 (now U.S. Pat. No. 7,320,805), entitled "CB2 RECEPTORS BLOCKS ACCUMULATION OF HUMAN HEPATIC MYOFIBROBLASTS: A NOVEL ANTIFIBROGENIC PATHWAY IN THE LIVER," filed Oct. 1, 2004 which claims the benefit of U.S. Provisional Application No. 60/508,178, filed Oct. 1, 2003, the entire disclosures of which are incorporated herein by reference for all purposes.

BACKGROUND

Liver fibrosis is the common response to chronic liver injury, ultimately leading to cirrhosis and its complications. The fibrogenic process is consecutive to intense proliferation and accumulation of hepatic myofibroblasts that synthesize fibrosis components and inhibitors of matrix degradation [1]. Hepatic myofibroblasts play a key role in the development of liver fibrosis associated with chronic liver diseases, and their removal by apoptosis contributes to the resolution of liver fibrosis. Better understanding of the molecular mechanisms and signaling pathways that govern hepatic myofibroblast functions is a prerequisite for the identification of antifibrotic targets that will enable to develop liver-directed antifibrotic drugs. Along these lines, currently recognized antifibrotic strategies include: (i) reduction of hepatic myofibroblast accumulation by molecules that block their proliferation or stimulate their apoptosis, and/or (ii) reduction of fibrosis by agents that inhibit extracellular matrix synthesis or enhance its degradation.

Cannabinoids are the main constituent of marijuana and include psychoactive molecules, such as $(-)\Delta^9$-tetrahydrocannabinol (THC), and non psychoactive substances, like cannabidiol. Endogenous natural cannabinoids have also been characterized, anandamide and 2-arachidonyl glycerol ([(5Z,8Z,11Z,14Z)-5,8,11,14-Eicosatetraenoic acid, 2-hydroxy-1-(hydroxymethyl)ethyl ester]), which are arachidonic acid-derived lipids [2, 23]. Cannabinoids display analgesic, antiemetic, vasorelaxing and anti-inflammatory properties, and stimulate food intake [3; 2]. They also exert antitumoral effects, mainly due to their antiproliferative and apoptotic properties [4]. Cannabinoid effects are mediated by activation of specific G protein-coupled receptors, CB1 and CB2 [5]. CB1 receptors are predominant in brain and are responsible for cannabinoid psychoactivity, whereas the peripheral CB2 receptors are mainly expressed in the immune system and are devoid of cannabinoid psychoactive effects [5]. Atypical CB receptors, distinct from CB1 and CB2 have been described in brain and in vascular endothelial cells.

SUMMARY

There are only few data concerning the hepatic action of cannabinoids. CB1 and CB2 receptors are not expressed in hepatocytes [6]. However, CB1 receptors are present in endothelial cells from hepatic artery, and their number increase in the cirrhotic liver [7]. The results presented herein demonstrate for the first time the hepatic expression of CB2 receptors in patients with chronic liver diseases, and the up-regulation of CB2 receptors in hepatic myofibroblasts. The results also show that CB2 receptors trigger potent growth inhibitory and apoptotic effects, two major antifibrogenic properties of hepatic myofibroblasts. Growth inhibition is mediated by induction of cyclooxygenase-2, and apoptosis results from CB2-dependent oxidative stress. These results indicate that, during chronic liver injury, activation of CB2 receptors can limit fibrogenesis originating from chronic liver diseases of any etiology (alcoholic, viral, toxic) by blocking accumulation of hepatic myofibroblasts.

Based upon these results, a variety of methods and compositions (e.g., pharmaceutical compositions) have been developed for treating diseases that are mediated by the activity or expression of CB2 receptors, including fibrosis associated with liver injury and disease. The methods are based, in part, on the finding that activation of CB2 receptors can reduce liver fibrogenesis associated with liver injury or disease. Thus, methods are provided for treating any hepatic diseases which result in hepatic fibrosis. The hepatic diseases include, but are not limited to, alcoholic liver cirrhosis, chronic viral hepatitis, non alcoholic steatohepatitis and primary liver cancer.

Some methods that are provided are methods of treating fibrosis during chronic liver injury and involves the use of cannabinoids. Other treatment methods involve the use of agonists of CB2 receptor. Still other methods involve the activation of CB2 receptors. Certain fibrosis treatment methods involve the up-regulation of CB2 receptors.

Also disclosed are methods for treating fibrosis during chronic liver injury which involve administering an effective amount of a cannabinoid to a patient having a liver injury. Other treatment methods involve administering an agent that activates a CB2 receptor to a patient having a liver injury. Still other methods of treating liver diseases comprise administering a composition comprising a non-selective agonist of CB2 and a selective antagonist of CB1 to a patient having a liver disease.

Screening methods to identify novel ligands (e.g., agonists) for CB2 receptors are also provided. Some of these screening methods involve (a) culturing hepatic myofibroblasts, (b) exposing the culture to a candidate ligand, (c) assessing the effect of the candidate ligands by an apoptosis, cell viability or cell proliferation assay, and (d) selecting a candidate ligand that has an effect in the assay.

Various compositions useful for treating fibrosis are also provided. Some compositions of this type contain one or more agonists of a CB2 receptor. The composition can also include a pharmaceutically acceptable carrier.

DETAILED DESCRIPTION

I. Definitions

Figure 1:
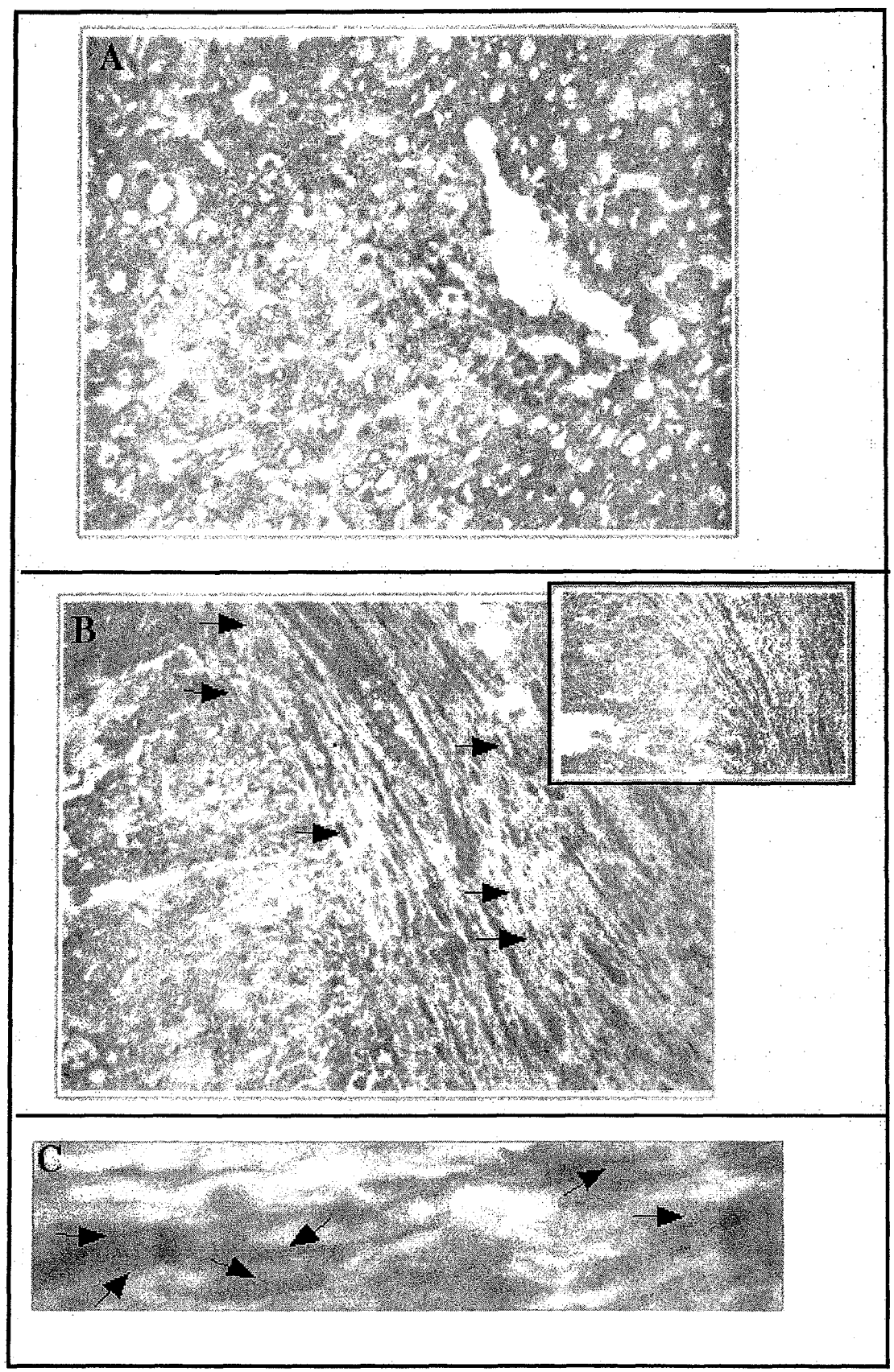
FIG. 1: Expression of CB2 receptor protein during chronic liver diseases. Representative distribution of CB2 receptor immunostaining on liver tissue sections obtained from biopsies of (A) normal liver and (B) active cirrhosis (Magnification ×200). Arrows indicate representative immunostaining of mesenchymal cells within and at the edge of the fibrotic septa. Inset shows negative control staining on active cirrhosis obtained after preadsorption of the anti-CB2 antibody (directed against CB2 receptor blocking peptide) with the CB2 synthetic peptide (Magnification ×200). (C) Representative double immunostaining for CB2 receptor (brown color) and smooth muscle alpha actin (red color) in cirrhotic liver (Magnification ×630). Arrows indicate cells immuno-positive for both CB2 receptor and smooth muscle alpha actin.

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

Various biochemical and molecular biology methods are well known in the art. For example, methods of isolation and purification of nucleic acids are described in detail in WO 97/10365, WO 97/27317, Chapter 3 of Laboratory Techniques in Biochemistry and Molecular Biology Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); Current Protocols in Molecular Biology, (Ausubel, F. M. et al., eds.) John Wiley & Sons, Inc., New York (1987-1993). Large numbers of tissue samples can be readily processed using techniques known in the art, including, for example, the single-step RNA isolation process of Chomczynski, P. described in U.S. Pat. No. 4,843,155.

As used herein, references to specific proteins (e.g., CB1 and CB2) can include a polypeptide having a native amino acid sequence, as well as variants and modified forms regardless of origin or mode of preparation. A protein that has a native amino acid sequence is a protein having the same amino acid sequence as obtained from nature (e.g., a naturally occurring CB1 or CB2). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including posttranslational modifications. A native sequence protein includes proteins following post-translational modifications such as glycosylation of certain amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook et al., Molecular Cloning: A Laboratory Manual, 3rd edition, Cold Spring Harbor Press, N.Y., (2001)).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols In Molecular Biology, Greene Publishing and Wiley-Interscience, New York (supplemented through 1999). Each of these references and algorithms is incorporated by reference herein in its entirety. When using any of the aforementioned algorithms, the default parameters for "Window" length. gap penalty, etc., are used. One example of algorithm that is suitable for determining percent sequence identity and sequence similarity is the BLAST algorithm, which is described in Altschul et al., J. Mol. Biol. 215:403-410 (1990).

Modified forms of a protein generally refer to proteins in which one or more amino acids of a native sequence have been altered to a non-naturally occurring amino acid residue. Such modifications can occur during or after translation and include, but are not limited to, phosphorylation, glycosylation, cross-linking, acylation and proteolytic cleavage.

The term "CB2 receptor" has its general meaning in the art [5], and may include naturally occurring CB2 receptors and variants and modified forms thereof. The term may also refer to fusion proteins in which a domain from CB2 that retains at least one CB2 activity is fused, for example, to another polypeptide (e.g., a polypeptide tag such as are conventional in the art). The CB2 receptor can be from any source, but typically is a mammalian (e.g., human and non-human primate) CB2, particularly a human CB2. An exemplary native CB2 amino acid sequence is provided in Accession No NP_001832.

CB2 activity" as used herein refers broadly to any biological activity associated with CB2. Thus, the term includes the specific binding of a ligand to CB2. The term also refers to various signal transducing activities of the receptor. Representative activities of CB2 include, ability to bind agonists such as those listed herein, activation of apoptosis, and inhibition of hepatic myofibroblast proliferation. Thus, the term "activate CB2" and other related terms refers to a process whereby one or more activities of CB2 are promoted or induced.

The term "CB1 receptor" has its general meaning in the art [5], and may include naturally occurring CB1 receptor and variants and modified forms thereof. The term also refers to fusion proteins in which a domain from CB1 that retains at least one CB1 activity is fused, for example, to another polypeptide (e.g., a polypeptide tag such as are conventional in the art). The CB1 receptor can be from any source, but typically is a mammalian (e.g., human and non-human primate) CB1, particularly a human CB1. CB1 receptors include for example, two isoforms: a long isoform (Accession No NP_057167) and a shorter one truncated in the NH2 terminal part corresponding to a splice variant (Accession No NP_149421).

"CB1 activity" as used herein refers broadly to any biological activity associated with CB1. Thus, the term includes the specific binding of a ligand to CB1. The term also refers to various signal transducing activities of the receptor. Representative activities of CB1 include, but are not limited to, ability to bind antagonists such as those listed herein and cannabinoid psychoactivity. Thus, the term "activate CB1" and other related terms refers to a process whereby one or more activities of CB1 are promoted or induced.

"Agonist" as used herein has its general meaning in the art, and refers to a compound natural or not which has the capability to activate a receptor. The term "selective CB2 receptor agonist" as used herein refers to a compound able to activate selectively CB2 receptors and not any other receptor such as CB1 receptors. The term "non selective CB2 receptor agonist" as used herein refers to compound natural or not which has the capability to activate CB2 receptors but also CB1 receptors.

"Antagonist" as used herein has its general meaning in the art, and refers to a compound natural or not which has the capability to inhibit the activation of a receptor. A "selective CB1 antagonist" is herein defined as a compound able to selectively inhibit the activation of CB1 receptors and not any other receptor such as CB2 receptors.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The terms "up-regulated and "activation" when used in reference to the expression of a nucleic acid such as a gene (e.g., CB2 receptor) refers to any process which results in an increase in production of a gene product or activity of the gene product. A gene product can be either RNA (including, but not limited to, mRNA, rRNA, tRNA, and structural RNA) or protein. Accordingly, gene up-regulation or activation includes those processes that increase transcription of a gene and/or translation of a mRNA. Examples of gene up-regulation or activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene up-regulation or activation can constitute, for example, inhibition of repression as well as stimulation of expression above an existing level. Examples of gene up-regulation or activation processes that increase translation include those that increase translational initiation, those that increase translational elongation and those that increase mRNA stability.

The level of gene expression, including the level of gene activation or up-regulation, can be quantitated utilizing a number of established techniques including, but not limited to, Northern-Blots, RNase protection assays (RPA), nucleic acid probe arrays, quantitative PCR (e.g., the so-called Taq-Man assays), dot blot assays and in-situ hybridization.

In general, gene up-regulation or activation comprises any detectable increase in the production of a gene product, preferably an increase in production of a gene product by at least 30, 40, 50 or 100%, in other instances from about 2- to about 5-fold or any integer therebetween, in still other instances between about 5- and about 10-fold or any integer therebetween, sometimes between about 10- and about 20-fold or any integer therebetween, in other instances between about 20- and about 50-fold or any integer therebetween, in yet other instances between about 50- and about 100-fold or any integer therebetween, and in still other instances 100-fold or more. The phrases up-regulation and activation are typically assessed relative to a control or baseline level.

As used herein a "control" or "baseline value" generally refers to a value (or ranges of values) against which an experimental or determined value (e.g., one determined for a patient sample as part of a diagnostic or prognostic test) is compared. Thus, in the case of CB2 up-regulation, the baseline value can be a value for CB2 activity or expression for a sample obtained from the same individual at a different time point. In other instances, the baseline value is a value determined for a control cell or individual, or a statistical value (e.g., an average or mean) established for a population of control cells or individuals. In the specific instance of CB2 up-regulation, the control can be a cell, individual or populations thereof for which CB2 levels would not be expected to be up-regulated. Thus, for instance, a control individual or control population can include healthy individuals, particularly those that have no liver injury. The population that serves as a control can vary in size, having as few as a single member, but potentially including tens, hundreds, or thousands of individuals. When the control is a large population, the baseline value can be a statistical value determined from individual values for each member or a value determined from the control population as an aggregate.

In the case of a screening assay, the control value can be a value for a control reaction that is conducted under conditions that are identical those of a test assay, except that the control reaction is conducted in the absence of a candidate agent whereas the test assay is conducted in the presence of the candidate agent. The control value can also be a statistical value (e.g., an average or mean) determined for a plurality of control assays. The control assay(s) upon which the control value is determined can be conducted contemporaneously with the test or experimental assay or can be performed prior to the test assay. Thus, the control value can be based upon contemporaneous or historical controls.

A difference is typically considered to be "statistically significant" if in general terms an observed value differs from a control or background value by more than the level of experimental error. A difference can be considered "statistically significant" if the probability of the observed difference occurring by chance (the p-value) is less than some predetermined level. As used herein a "statistically significant difference" refers to a p-value that is <0.05, preferably <0.01 and most preferably <0.001.

II. Overview

A variety of methods for treating fibrosis associated with liver injury are provided. The methods are based, in part, upon the recognition that hepatic myofibroblasts are central for the development of liver fibrosis associated with chronic liver diseases and that blocking their accumulation can prevent fibrogenesis. Cannabinoids act via two receptors, CB1, responsible for their psychoactive effects, and CB2, expressed in peripheral tissues. In liver biopsies from patients with active cirrhosis of various etiologies, immunohistochemistry showed the presence of CB2 receptors in non-parenchymal cells located within and at the edge of fibrous septa. In contrast, no expression of CB2 receptors was detected in normal human liver. CB2 receptors were expressed in human hepatic myofibroblasts, as shown by immunocytochemistry in liver biopsies and in cultured cells, and functional, as evidenced in GTPγS binding assays. Activation of CB2 receptors led to growth inhibition and apoptosis of cultured human hepatic myofibroblasts via a CB2-dependent process, as demonstrated using selective CB2 agonists (JWH-015 and cannabidiol) and antagonist (SR 144528). The antiproliferative effect of THC was blunted by ibuprofen, a cyclooxygenase (COX) inhibitor and NS 398 ([N-(2-cyclohexyloxy-4-nitrophenyl)methane sulfonamide] from Biomol Research Labs (Plymouth Meeting, Pa.); see, e.g., Liu X. H., et al. (1998) Cancer Res. 58: 4245-4249), a selective COX-2 inhibitor. Accordingly, THC induced COX-2. In contrast, THC-induced apoptosis was blocked by the antioxidants N-acetyl cysteine and EUK 8 (see, e.g, Pucheu, S., et al. (1996) Cardiovasc. Drugs Ther. 10:331-339), and THC generated production of reactive oxygen species.

The results demonstrate that the liver is a target of cannabinoids during chronic liver diseases. Indeed, CB2 receptors are up-regulated in hepatic myofibroblasts, and their activation reduces accumulation of these cells by triggering potent growth inhibitory and apoptotic effects. These results provided herein thus indicate that activation of CB2 receptors can limit liver fibrogenesis during chronic liver injury. The results also indicate that a CB2 receptor-based antifibrotic strategy can be used which is devoid of undesirable CB1-mediated psychotropic effects.

Compositions useful in treating various diseases associated with liver injury are also provided, as are methods of identifying agents that modulate (e.g., increase) the activity of CB2 and which can be utilized in the development of new pharmaceutical compositions.

III. Treatment Methods, Pharmaceutical Compositions and Methods of Administration A. General A variety of pharmaceutical compositions are provided. Some compositions comprise one or more active ingredients that activate the CB2 receptor or up-regulate the expression of CB2 receptors. Certain compositions thus include one or more agonists of the CB2 receptor. The pharmaceutical compositions that are provided are useful in treating various diseases that are mediated by CB2 receptors, including treatment of fibrosis associated with liver injury (e.g., cirrhosis). The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

B. Composition

The pharmaceutical compositions used for prophylactic or therapeutic treatment comprise an active therapeutic agent, for example, an agent that activates the CB2 receptor or up-regulates the expression of CB2 receptors. Examples of such agents include various agonists. The agonists can be selective for CB2 or non-selective for CB2. One general class of agonists are the cannabinoids. Some compositions include a plurality of agonists (selective and/or non-selective). Still other compositions that are provided include a combination of one or more CB2 agonists and one or more CB1 antagonists.

One specific example of a selective agonist that can be utilized in certain compositions is palmitoylethanolamide [N-(2-Hydroxyethyl)hexadecanamide] (see, e.g., Facci, et al. (1995) Proc. Natl. Acad. Sci. USA 92:3376), which is commercially-available from Tocris. The chemical structure is as follows:

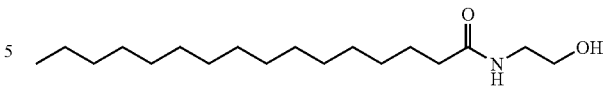

The molecule referred to as JWH-133 [(6aR,10aR)-3-(1,1-dimethylbutyl)-6a,7,10,10a-tetrahydro-6,6,9-trimethyl-6H-dibenzo[b,d]pyran] is another exemplary selective agonist that can be incorporated into a composition (see, e.g., Huffman et. al. (1999) Bioorg. Med. Chem. 7:2905). The structure of JWH-133 is provided below:

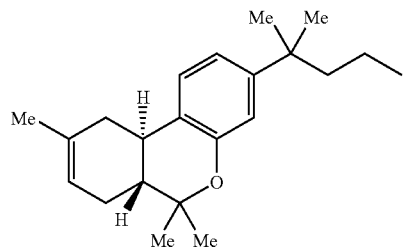

Other selective CB2 receptor agonists that can be used include those disclosed in published U.S. Patent Application US2004034090, entitled "3-Arylindole derivatives and their use as CB2 receptor agonists." Agonists of this class have the following general structure:

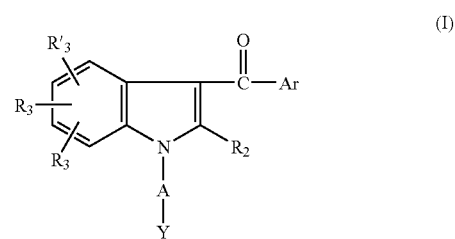

in which:

Ar represents:
a) a phenyl mono-, di- or trisubstituted by one or more groups chosen from: a halogen atom, a (C1-C4)alkyl, a trifluoromethyl, an amino, a nitro, a hydroxyl, a (C1-C4) alkoxy, a (C1-C4)alkylsulphanyl or a (C1-C4)alkylsulphonyl;
b) a naphthyl which is unsubstituted or substituted once or twice by a halogen atom, a (C1-C4)alkyl or a trifluoromethyl;

A represents a C2-C6 alkylene radical;

Y represents a group chosen from SR4, SOR4, SO2R4, SO2NR5R6, N(R7)SO2R4, OR4 or NR7SO2NR5R6;

R1, R3 and R13 represent, each independently of one another, hydrogen, a hydroxyl, a halogen atom, a (C1-C4) alkyl, a trifluoromethyl or a (C1-C4)alkoxy;

R2 represents hydrogen or a (C1-C4)alkyl;

R4 represents a (C1-C4)alkyl or a trifluoromethyl

R5 and R6 each independently represent hydrogen or a (C1-C4)alkyl; and

R7 represents hydrogen or a (C1-C4)alkyl.

Still other classes of agonists that can be included in the compositions include, but are not limited to, those described in 1) U.S. Pat. Nos. 6,013,648 and 5,605,906; 2) Published PCT applications WO0132169, WO0128497 and WO9618391; 3) published U.S. Patent Applications US2004077643 and US2002173528; and 4) EP1374903, each of which is incorporated herein by reference in its entirety for all purposes.

Various non-selective agonists of CB2 can also be utilized in certain methods and incorporated into pharmaceutical compositions. For instance, the composition can include CP 55,940 [(−)-cis-3-[2-Hydroxy-4-(1,1-dimethylheptyl)phenyl]-trans-4-(3-hydroxypropyl)cyclohexanol] (Wiley et al (1995) Neuropharmacology 34:669), which is available from Tocris. The compound has the following structure:

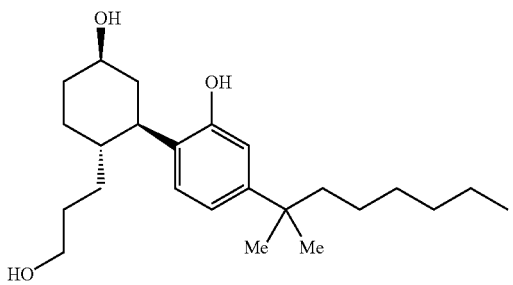

Hu 210 is another one example of a suitable non-selective agonist. HU 210 [(6aR)-trans-3-(1,1-Dimethylheptyl)-6a,7,10,10a-tetrahydro-1-hydroxy-6,6-dimethyl-6H-dibenzo[b,d]pyran-9-methanol] (Mechoulam et al (1988) 44 762) has the following structure:

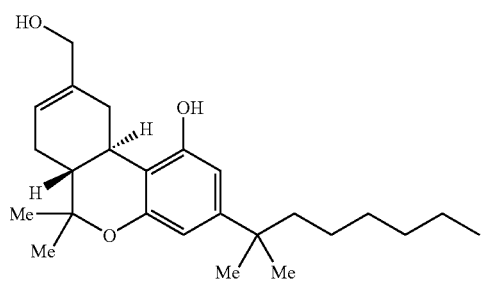

Another useful non-selective agonist of CB2 is WIN 55, 212-2 [(R)-(+)-[2,3-Dihydro-5-methyl-3-(4-morpholinylmethyl)pyrrolo[1,2,3-de]-1,4-benzoxazin-6-yl]-1-naphthalenylmethanone mesylate] (Martellotta et al (1998) Neuroscience 85 327). The structure of WIN 55, 212-2 is as follows:

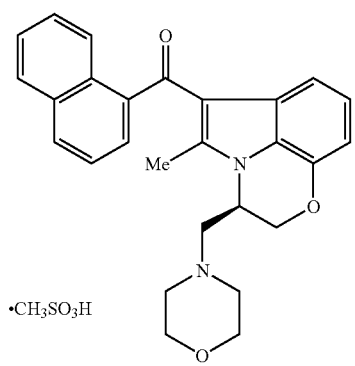

Compositions that are provided herein can also incorporate Anandamide [N-(2-Hydroxyethyl)-5Z,8Z,11Z,14Z-eicosatetraenamide] (Pertwee (1999) Curr. Med. Chem. 6 635), which has the structure as follows:

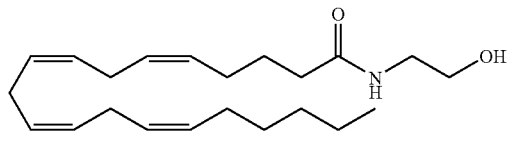

As noted above, some compositions include a non selective agonist of CB2 receptor in combination with a selective antagonist of CB1 receptor. Such suitable antagonists of CB1 receptor include, but are not limited to, SR141716, AM 281, AM 251, the substituted amides described in WO03/077847, the substituted aryl amides described in WO03/087037, the substituted imidazoles described in WO03/063781, bicyclic amides described in WO03/086288, the terphenyl derivatives described in WO 03/084943, the aryl-benzo[b]thiophene and benzo[b]furan compounds respectively described in U.S. Pat. Nos. 5,596,106 and 5,747,524, the azetidine derivatives described in FR2805817, 3-amino-azetidine described in FR2805810, or the 3-Substituted or 3,3-disubstituted 1-(di-((hetero)aryl)-methyl)-azetidine derivatives described in FR2805818.

N-pipéridino-5-(4-chlorophényl)-1-(2,4-dichlorophényl)-4-méthylpyrazole-3-carboxamide, known commercially as SR141716 or rimonabant, and its preparation are described in the European patent application EP656354-A1 and is represented by the formula as follows:

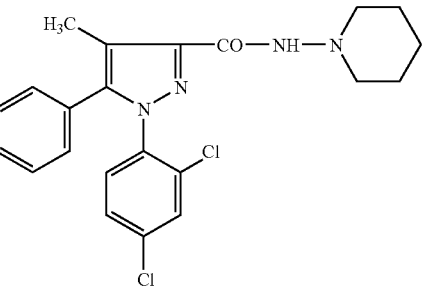

N-(piperidin-1-yl)-1-(2,4-dichlorophenyl)-5-(4-iodophenyl)-4-methyl-1H-pyrazole-3-carboxamide, known commercially as AM251, has the structure described below:

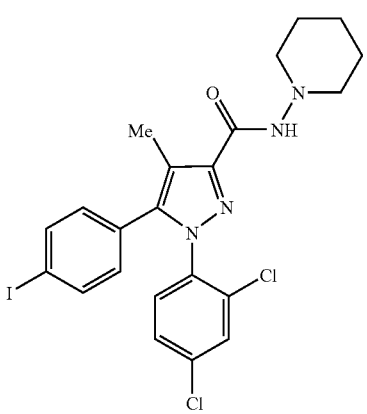

1-(2,4-Dichlorophenyl)-5-(4-iodophenyl)-4-methyl-N-4-morpholinyl-1H-pyrazole-3-carboxamide, known commercially as AM281, has the structure as follows:

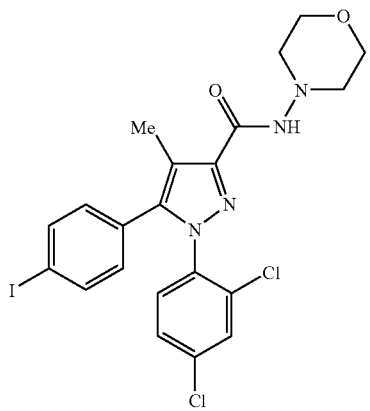

Certain compositions that are provided include at least one agonist of CB2 receptor (selective or not) and at least one selective antagonist of CB1 receptor. Some compositions, for example, comprise a least one agonist of CB2 receptor (selective or not) in combination with SR141716.

The compositions, in addition to the active ingredient(s) such as those just listed, may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation may also include other carriers, adjuvants, or non-toxic, nontherapeutic, nonimmunogenic stabilizers, excipients and the like. The compositions may also include additional substances to approximate physiological conditions, such as pH adjusting and buffering agents, toxicity adjusting agents, wetting agents, detergents and the like.

Further guidance regarding formulations that are suitable for various types of administration can be found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

C. Administration

The compositions containing the CB2 agonist(s) can be administered for prophylactic and/or therapeutic treatments. The active ingredient (e.g., CB2 receptor agonist(s)) in the pharmaceutical composition generally is present in an "effective amount." By an "effective amount" of a pharmaceutical composition is meant a sufficient, but nontoxic amount of the agent to provide the desired effect. The term refers to an amount sufficient to treat a subject (e.g., a mammal, particularly a human). Thus, the term "therapeutic amount" refers to an amount sufficient to remedy a disease state or symptoms, by preventing, hindering, retarding or reversing the progression of the disease or any other undesirable symptoms whatsoever. The term "prophylactically effective" amount refers to an amount given to a subject that does not yet have the disease, and thus is an amount effective to prevent, hinder or retard the onset of a disease.

In therapeutic applications, compositions are administered to a patient already suffering from a disease, as just described, in an amount sufficient to cure or at least partially arrest the symptoms of the disease and its complications. An appropriate dosage of the pharmaceutical composition is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example. What constitutes an effective dose also depends on the nature and severity of the disease or condition, and on the general state of the patient's health.

In prophylactic applications, compositions containing, for example CB2 receptor agonists, are administered to a patient susceptible to or otherwise at risk of a disease mediated by CB2 receptors (e.g. fibrosis formation). Such an amount is defined to be a "prophylactically effective" amount or dose. In this use, the precise amounts again depends on the patient's state of health and weight.

In both therapeutic and prophylactic treatments, the agonist contained in the pharmaceutical composition can be administered in several dosages or as a single dose until a desired response has been achieved. The treatment is typically monitored and repeated dosages can be administered as necessary. Compounds of the invention may be administered according to dosage regimens established whenever activation of CB2 receptors is required.

The daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. It will be understood, however, that the specific dose level and frequency of dosage for any particular patient may be varied and will depend upon a variety of factors including the activity of the specific compound employed, the metabolic stability, and length of action of that compound, the age, the body weight, general health, sex, diet, mode and time of administration, rate of excretion, drug combination, the severity of the particular condition, and the host undergoing therapy.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, and intrathecal methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

If desired, it is possible to formulate solid or liquid formulations in an enteric-coated or otherwise protected form. In the case of liquid formulations, the formulation can be mixed or simply coadministered with a protectant, such as a liquid mixture of medium chain triglycerides, or the formulation can be filled into enteric capsules (e.g., of soft or hard gelatin, which are themselves optionally additionally enteric coated). Alternatively, solid formulations comprising the polypeptide can be coated with enteric materials to form tablets. The thickness of enteric coating on tablets or capsules can vary. Typical thickness range from 0.5 to 4 microns in thickness. The enteric coating may comprise any of the enteric materials conventionally utilized in orally administrable pharmaceutical formulations. Suitable enteric coating materials are known, for example, from *Remington's Pharmaceutical Sciences*, Mace Publishing Company, Philadelphia, 17th ed. (1985); and *Hagars Handbuch der Pharmazeutischen Praxie*, Springer Verlag, 4$^{th}$ ed., Vol. 7a (1971).

Another delivery option involves loading the composition into lipid-associated structures (e.g., liposomes, or other lipidic complexes) which may enhance the pharmaceutical characteristics of the polypeptide component of the composition. The complex containing the composition may subsequently be targeted to specific target cells by the incorporation of appropriate targeting molecules (e.g., specific antibodies or receptors). It is also possible to directly complex the polypeptide with a targeting agent.

Compositions prepared for intravenous administration typically contain 100 to 500 ml of sterile 0.9% NaCl or 5% glucose optionally supplemented with a 20% albumin solution and 100 to 500 mg of a polypeptide of the invention. Methods for preparing parenterally administrable compositions are well-known in the art and described in more detail in various sources, including, for example, *Remington's Pharmaceutical Science*, Mack Publishing, Philadelphia, Pa., 17th ed., (1985).

Particularly when the compositions are to be used in vivo, the components used to formulate the pharmaceutical compositions of the present invention are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

IV. Methods for Identifying CB2 Modulators

A variety of screening methods can be utilized to identify modulators (e.g., agonists or antagonists) of CB2. Because the current inventors have found that activation of CB2 activity plays an important role in inhibiting the growth of human hepatic myofibroblasts, agonists identified in the screening methods can be used, for example, as candidate agents in the treatment of undesirable fibrosis associated with liver disease.

A. Binding Assays

Competition binding assays can also be used in the screening methods. In assays of this type, a known ligand of CB2 such as those listed above, is combined with CCR1 (or a variant or fragment thereof that retains binding activity) in the presence of a test agent. The extent of binding between the known ligand and CB2 in the presence of the test agent is compared with the level of ligand binding in a control, typically a similar assay conducted in the absence of the test agent. A difference (e.g., a statistically significant difference) between the test and control assays is an indication that the test agent is a modulator of CB2 activity. An increase in binding of the known ligand is an indication that the test agent is an agonist. A decrease in binding of the known ligand, in contrast, is an indication that the test agent is an antagonist.

The binding assays can be conducted as cell-based assays, which use cells that naturally express CB2 (e.g., cultured hepatic cells) or cells that have been stably or transiently transfected and thus express CB2. The cells are maintained under conditions appropriate for expression of the receptor and are contacted with the test agent and the known ligand under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells. Detection of binding or complex formation can be detected directly or indirectly. For example, the test agent or the known ligand can be labeled with a suitable label (e.g., fluorescent label, chemiluminescent label, isotope label, enzyme label, and the like) and binding can be determined by detection of the label.

Other binding assays, however, are non-cellular assays. Such assays can be conducted by immobilizing CB2 to a support, for example, and the contacting the immobilized receptor with a composition containing the test agent. Formation of complex can be detected and optionally quantified as just described. The CB2 protein in such assays may be a fusion protein that includes a CB2 domain that retains an activity of CB2 and a tag (e.g., any of the polypeptide tags listed supra). In these assays, the fusion protein is immobilized to a support via the tag (e.g., an antibody deposited on the support that binds the tag). Further guidance regarding receptor binding assays is provided, for example, by Parce et al., 1989, *Science* 246: 243-247; and Owicki et al., 1990, *Proc. Nat'l Acad. Sci. USA* 87: 4007-4011.

B. Biological Assays

Other screening assays that are provided are designed not only to determine whether a test agent binds CB2, but also determine if the test agent can modulate a CB2 activity. Because CB2 is a G-protein coupled receptor, the binding of a ligand to CB2 can result in signaling, and the activity of G proteins as well as other intracellular signaling molecules can be stimulated. Examples of biological activities mediated by CB2 include stimulation of apoptosis and cell death, and inhibition of cell growth and cell proliferation. The induction of a biological function by a test agent can be monitored using any suitable method. The capacity of a test agent to modulate the activity of CCR1 can be determined in the presence of a ligand. The examples provide further details on certain (e.g., apoptosis) assays that can be utilized in the screening methods.

1. Exemplary Cell Proliferation Assays

Cellular proliferation assays can be conducted in a variety of different ways, including, for example: actual cell counting, clonogenic assays, measuring metabolic activity, measuring DNA synthesis and/or measuring the level of molecules that regulate cell cycle (e.g., CDK kinase assays). A brief summary of these approaches follows. For a general review of some of these approaches, see for example, Roche Molecular Biochemicals, "Apoptosis and Cell Proliferation", $2^{nd}$ Revised edition, pages 66-114, which is incorporated herein by reference in its entirety for all purposes. Regardless of the particular approach taken for determining cell proliferation, certain screening methods that involve monitoring cell proliferation involve contacting a cell or cell population expressing CB2 in the presence of a test agent (optionally in the presence of a known CB2 ligand) and then determining the level of cell proliferation in the presence of the test compound. The determined level of cell proliferation is then compared with the level of cell proliferation in the absence of the test agent. An increase in cell proliferation in the presence of the test agent indicates that the test agent is an inhibitor of CB2, whereas a decrease in cell proliferation indicates that the test agent is an activator of CB2.

One approach to detect cell proliferation is simply to count the number of cells using a cell counting device such as a hemacytometer. In the clonogenic assay approach, a defined number of cells are plated out onto a suitable media and the number of colonies that are formed after a defined period of time are determined. The clonogenic approach can be somewhat cumbersome for large number of samples and for cells that divide only a few times and then become quiescent.

A number of different assays for measuring metabolic activity are available. One approach is to incubate the cells with a tetrazolium salt (e.g., MTT, XTT or WST-1), which becomes cleaved during cellular metabolism to form a colored formazan product. Further guidance regarding assays of this type are provided by Cook, J. A. and Mitchell, J. B. (1989) Anal. Biochem. 179:1; Roehm, N. W. et al. (1991) J. Immunol. Methods 142:257; Slater, T. F., et al. (1963) Biochem. Biophys. Acta 77:383; Berridge, M. V. and Tan, A. S. (1993) Arch. Biochem. Biophys. 303:474; Cory, A. H., et al. (1991) Cancer Commun. 3:207; Jabbar, S. A. B., et al. (1989) Br. J. Cancer 60: 523; and Scudiero, E. A., et al. (1988) Cancer Res. 48, 4827, each of which is incorporated herein by reference in its entirety for all purposes. A variety of kits for performing such assays are available from Roche Molecular Biochemicals. Other assays in this class involve the measurement of ATP and involve detecting the formation of luminescence formed via the activity of luciferase. Such assays are commercially available from Perkin Elmer (see, e.g., ATPlite™ Assay kits).

Because DNA is replicated during cell proliferation, assays that provide a measure of DNA replication also provide an useful measure of cell proliferation. Assays of this type typically involve adding labeled DNA precursors to a cell culture. Cells that are about to divide incorporate the labeled nucleotide into their DNA. Some approaches utilize tritiated thymidine ([3H]-TdR) and measure the amount of incorporated tritiated thymidine using liquid scintillation counting. To avoid using radioactive compounds, other assays utilize the thymidine analog 5-bromo-2'deoxy-uridine (BrdU), which becomes incorporated into DNA just like thymidine. Incorporated BrdU can be detected quantitatively using a cellular immunoassay that utilizes monoclonal antibodies directed against BrdU. Commercial kits for performing such assays are available from a number of sources including Roche Molecular Biochemicals.

2. Apoptosis/Cell Death Assays

A variety of different parameters can be monitored to detect cell death and apoptosis. Examples of such parameters include, but are not limited to, monitoring activation of cellular pathways for toxicological responses by gene or protein expression analysis, DNA fragmentation; changes in the composition of cellular membranes, membrane permeability, activation of components of death-receptors or downstream signaling pathways (e.g., caspases), generic stress responses, NF-kappaB activation and responses to mitogens. Specific examples of such assays follow.

Morphological Changes Apoptosis in many cell types is correlated with altered morphological appearances. Examples of such alterations include, but are not limited to, plasma membrane blebbing, cell shape change, loss of substrate adhesion properties. Such changes are readily detectable with a light microscope. Cells undergoing apoptosis can also be detected by fragmentation and disintegration of chromosomes. These changes can be detected using light microscopy and/or DNA or chromatin specific dyes.

Altered Membrane Permeability: Often the membranes of cells undergoing apoptosis become increasingly permeable. This change in membrane properties can be readily detected using vital dyes (e.g., propidium iodide and trypan blue). Similarly, dyes can be used to detect the presence of necrotic cells. For example, certain methods utilize a green-fluorescent LIVE/DEAD Cytotoxicity Kit #2, available from Molecular Probes. The dye specifically reacts with cellular amine groups. In necrotic cells, the entire free amine content is available to react with the dye, thus resulting in intense fluorescent staining. In contrast, only the cell-surface amines of viable cells are available to react with the dye. Hence, the fluorescence intensity for viable cells is reduced significantly relative to necrotic cells (see, e.g., Haugland, 1996 Handbook of Fluorescent Probes and Research Chemicals, 6th ed., Molecular Probes, Oreg.).

Dysfunction of Mitochondrial Membrane Potential: Altered or defective mitochondrial activity can result in mitochondrial collapse called the "permeability transition" or mitochondrial permeability transition. Proper mitochondrial functioning requires maintenance of the membrane potential established across the membrane. Dissipation of the membrane potential prevents ATP synthesis and thus halts or restricts the production of a vital biochemical energy source. Consequently, a variety of assays designed to assess toxicity and cell death involve monitoring the effect of a test agent on mitochondrial membrane potentials or on the mitochondrial permeability transition. One approach is to utilize fluorescent indicators (see, e.g., Haugland, 1996 Handbook of Fluorescent Probes and Research Chemicals, 6th ed., Molecular Probes, Oreg., pp. 266-274 and 589-594). Various non-fluorescent probes can also be utilized (see, e.g., Kamo et al. (1979) J. Membrane Biol. 49:105). Mitochondrial membrane potentials can also be determined indirectly from mitochondrial membrane permeability (see, e.g., Quinn (1976) The Molecular Biology of Cell Membranes, University Park Press, Baltimore, Md., pp. 200-217). Further guidance on methods for conducting such assays is provided in PCT publication WO 00/19200 to Dykens et al.

Caspase Activation Some assays for apoptosis are based upon the observation that caspases are induced during apoptosis. Induction of these enzymes can be detected by monitoring the cleavage of specifically-recognized substrates for these enzymes. A number of naturally occurring and synthetic protein substrates are known (see, e.g., Ellerby et al. (1997) J. Neurosci. 17:6165; Kluck, et al. (1997) Science 275:1132; Nicholson et al. (1995) Nature 376:37; and Rosen and Casciola-Rosen (1997) J. Cell Biochem. 64:50). Methods for preparing a number of different substrates that can be utilized in these assays are described in U.S. Pat. No. 5,976,822.

Cytochrome c Release: In healthy cells, the inner mitochondrial membrane is impermeable to macromolecules. Thus, one indicator of cell apoptosis is the release or leakage of cytochrome c from the mitochondria. Detection of cytochrome c can be performed using spectroscopic methods because of the inherent absorption properties of the protein. Alternatively, the protein can be detected using standard immunological methods (e.g., ELISA assays) with an antibody that specifically binds to cytochrome c (see, e.g., Liu et al. (1996) Cell 86:147).

Assays for Cell Lysis: When cells die they typically release a mixture of chemicals, including nucleotides, and a variety of other substances (e.g., proteins and carbohydrates) into their surroundings. Some of the substances released include ADP and ATP, as well as the enzyme adenylate cyclase which catalyzes the conversion of ADP to ATP in the presence of excess ADP. Thus, certain assays involve providing sufficient ADP in the assay medium to drive the equilibrium towards the generation of ATP which can subsequently be detected via a number of different means. One such approach is to utilize a luciferin/luciferase system that is well known to those of ordinary skill in the art in which the enzyme luciferase utilizes ATP and the substrate luciferin to generate a photometrically detectable signal. Further details regarding certain cell lysis assays are set forth in PCT publication WO 00/70082.

C. Test Agents

A variety of different types of agents can be screened for the ability to modulate the activity CB2. The agents can be agonists or antagonists. The agents can be include, for example, antibodies, peptides or small molecules, hormones, naturally occurring molecules, or molecules from existing repertoires of chemical compounds synthesized by the pharmaceutical industry. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in PCT Publications WO 95/12608, WO 93/06121, WO 94/08051, 95/35503 and WO 95/30642. Peptide libraries can also be generated by phage display methods. See, e.g., Devlin, WO 91/18980. Compounds to be screened can also be obtained from the National Cancer Institute's Natural Product Repository, Bethesda, Md., as well as a number of other commercial sources. The agents to be screened can also be agonist antibodies and antagonist antibodies. A general review of methods for preparing libraries is provided by Dolle and Nelson (*J. Combinatorial Chemistry* 1: 235-282 (1999)).

The following examples are provided to illustrate certain aspects of the methods and compositions that are provided but should not be construed to limit the scope of the claimed invention.

Example

I. Methods

Materials. Culture media and reagents were from Gibco (Invitrogen, France). Fetal calf serum was from J Bio Laboratories (France). Pooled human AB positive serum was supplied by the National Transfusion Center. N-acetyl-Asp-Glu-Val-Asp-7-amino-4-trifluoromethyl coumarin (AC-DEVD-AFC) fluorogenic substrate and NS 398 were from Biomol and PDGF-BB from Preprotech Inc (Tebu, France). 2'.7'-dichlorofluorescein diacetate (DCFH-DA) was from Molecular Probes (Interchim, France), Z-val-Ala-Asp (OCH3)-Fluoromethyl ketone (ZVAD-fmk) from R&D Systems, 4,6-diamidino-2-phenylindole (DAPI) from Biovalley (France), CellTiter 96 AQ$_{ueous}$ One Solution reagent from Promega (France) and Apoptotic DNA Ladder Kit from Roche (Germany). N-acetyl-cysteine, (Sigma) was dissolved in PBS and buffered with NaOH to pH 7.4 prior to use. [$^{35}$S] GTPγS was from ICN (France). EUK8 (see, e.g., Pucheu, S. (1996) Cardiovasc. Drugs Ther. 10:331-339) was kindly provided by Eukarion Inc (Bedford, USA). The rabbit anti-CB2 receptor antisera (raised against residues 20-33 of the human CB2 receptor) and CB2 blocking peptide (residues 20-33 of the human CB2 receptor, having the amino acid sequence NPMKDYMILSGPQK; SEQ ID NO:1) were from Cayman (Spibio, France). SR 144528 ({N-[1S)-endo-1,3,3,-trimethyl bicyclo[2.2.1]heptan-2-yl]-5-(choloro-3-methylphenyl)-1-(4-methyl-benzyl)-pyrazole-3-carboxamide) and SR 141716A (N-(piperidin-1-yl)-5-(4-chlorophenyl)-1-(2,4-dichlorophenyl)-4-methylpyrazol-3-carboxamide hydrochloride) (8) were kindly provided by Sanofi (Montpellier, France) (see, also EP 656354-A1). ACEA (arachidonyl-2'-chloroethylamide [N-(2-Chloroethyl)-5Z,8Z,11Z,14Z-eicosatetraenamide; see reference [5]) and JWH-015 ([(2-Methyl-1-propyl-1H-indol-3-yl)-1-naphthalenylmethanone]; see reference [5]) were purchased from Tocris (Fisher Bioblock, France). Δ9-tetrahydrocannabinol (THC) ([6a,7,8,10a-Tetrahydro-6,6,9-trimethyl-3-(pentyl-5,5,5-d3)-6H-dibenzo (b,d)pyran-1-ol]) was from Sigma (France).

Human liver specimen. Snap frozen surgical liver resections from 13 patients (8 men, 5 women, mean age 55 years, 39-72 range years) were retrospectively studied. Normal liver samples were collected from 3 women undergoing hepatic resection for colorectal metastasis (n=3). Cirrhotic samples were obtained from 8 livers of patients undergoing liver transplantation and from 2 patients undergoing hepatic resection for hepatocellular carcinoma. Cirrhosis was consecutive to chronic HCV (n=1) or HBV (n=2) infections, primary biliary cirrhosis (n=1), alcoholic liver disease (n=4), or Wilson disease (n=1) and remained cryptogenic in 1 case. This study conformed to the ethical regulations imposed by French legislation.

Immunohistochemical detection of CB2 receptors in normal and cirrhotic livers. Frozen sections (5-7 µm) were air-dried and fixed in ice-cold acetone for 10 minutes at −20° C. Non specific binding was blocked by preincubating sections 1 hr at room temperature with 20% AB-human serum in 50 mM Tris-buffered saline (TBS) pH 7.6. Excess antiserum was removed, and sections were further incubated over night at 4° C. with a rabbit polyclonal antisera to human CB2 receptor, diluted 1/350 in antibody diluent (Dakopatts, France). After rinsing 3 times in TBS, sections were incubated for 45 min at room temperature with mouse monoclonal anti-rabbit immunoglobulin G antibodies, diluted 1/50 (Dakopatts, France), rinsed 3 times in TBS, further incubated for 30 min at room temperature with rabbit anti-mouse immunoglobulin antibodies (Dakopatts, France), diluted 1/50, and then processed using the alkaline phosphatase-anti-alkaline phosphatase (APAAP) complex immunoenzymatic method. Briefly, after washing 3 times in TBS, slides were incubated for 30 min at room temperature with the APAAP complex, diluted 1/25. After rinsing twice in TBS pH 7.6 and once in TBS pH 8.2, sections were revealed using naphthol AS-TR phosphate-Fast Red TR (Sigma, France) in the presence of levamisole, in order to block endogenous phosphatase activity. Slides were counterstained with aqueous haematoxylin. To confirm the specificity of the primary antibody, controls included preadsorption of the primary antibody with the corresponding synthetic peptide (100 µg/ml, for 1 hr at room temperature) or omission of the primary antibody.

In order to determine whether hepatic myofibroblasts express CB2 protein, double immunostaining of CB2 and smooth muscle α-actin was performed. Sections were first processed for CB2 immunostaining using a standard three-stage biotin-streptavidin immunoperoxidase method. Briefly endogenous peroxidase was quenched by incubation of the acetone fixed sections in TBS/0.3% H202 for 30 min then washed in TBS. Non specific binding was blocked by preincubating sections 30 min with TBS/20% AB-human serum. Sections were then incubated for 15 min in avidin followed by 15 min in biotin (Vector Laboratories, Avidin/Biotin blocking kit), and further incubated over night at 4° C. with the anti CB2 antisera. Subsequently, sections were washed in TBS and incubated successively with the secondary antibody biotinylated goat anti-rabbit (Dakopatts) (1/500) and streptavidin-horseradish peroxidase complex (1/50) (Pierce, Perbio, Interchim, France), 30 min each. Peroxidase activity was revealed using metal-enhanced diaminobenzidine (DAB) substrate (Pierce). All steps were carried out at room temperature unless otherwise mentioned. Immunostaining for smooth muscle α-actin was then processed using the APAAP method described above, with a 1/5000 dilution of a monoclonal antibody to smooth muscle α-actin (Sigma, France). Slides were counterstained with aqueous haematoxylin. Single and double staining were visualized by bright-field photomicrographs on an Axioplan microscope (Zeiss, Oberkochen, Germany), equipped with a digital imaging system (Hamamatsu 3CCD color camera, Hamamatsu Photonics, France).

Isolation and culture of human hepatic myofibroblasts. Human hepatic myofibroblasts were obtained by outgrowth of explants prepared from surgical specimens of normal liver, as previously described [10]. This procedure was performed in accordance with ethical regulations imposed by the French legislation. Cells were cultured in Dulbecco's modified Eagle's medium (DMEM) containing 10% serum (5% fetal calf serum, and 5% pooled human AB-positive serum, DMEM 5/5) and were used between the third and seventh passage. Experiments were performed on cells that were made quiescent by a 48 hrs incubation in serum-free Waymouth medium. The myofibroblastic nature of the cells was evaluated as previously described [9]. The cultures were found to express two markers of rat hepatic myofibroblasts, fibulin-2 and interleukin-6, and not the protease P100, a marker for rat hepatic stellate cells [9].

Culture of CHO cells overexpressing CB1 or CB2 receptors. Cells were kindly provided by Sanofi (Montpellier, France) and were cultured in DMEM medium containing 5% SVF and 20 ng/ml gentamicin. Experiments were performed on cells that were made quiescent by a 48 hrs incubation in serum-free Waymouth medium containing 20 ng/ml gentamicin.

RNA Preparation and RT-PCR. Total RNA was extracted from confluent quiescent cells in 100 mm dishes, using RNeasy kit (Qiagen, France). cDNA was synthesized from 2 µg of total RNA by reverse transcription for 1 h at 37° C. using 200 units of M-MLV reverse transcriptase (Invitrogen, France), in a 20 µl reaction mixture containing 0.05 µg/µl oligo (dT)$_{12-18}$ (SEQ ID NO:2) primers (Invitrogen, France), 0.5 mM dNTPs (Promega, France) and 10 mM dithiothreitol in first strand buffer (Invitrogen, France). To check for eventual genomic DNA contamination, RT controls were performed in the same conditions without reverse transcriptase. PCRs were performed with 2 µl of the reverse transcription reaction using 1.25 units of AmpliTaq Gold DNA polymerase (Applied Biosystems, France) and the corresponding buffer supplemented with 2 mM MgCl2, 0.2 mM dNTPs, and 25 pmol of each primer in a total volume of 50 µl. 40 PCR cycles were carried out in a GeneAmp 2700 thermalcycler (Applied Biosystems, France), each cycle consisting of denaturation at 95° C. for 45 s, annealing at 58° C. for 45 s, and extension at 72° C. for 30 s, with the first cycle containing an extended denaturation period (10 min) for the activation of the polymerase and the last cycle containing an extended elongation period (10 min). Oligonucleotide primers (MWG Biotech, France) for CB2 were as follows: CB2 sense primer 5'-TTTCCCACTGATC-CCCAATG-3' (SEQ ID NO:3) and CB2 antisense primer, 5'-AGTTGATGAGGCACAGCATG-3' (SEQ ID NO:4), and the predicted PCR product of 337 bp. PCR amplified products were analyzed on a 1.5% agarose gel and blotted onto Hybond-N+ membrane (Amersham Pharmacia Biostech, France). After a prehybridization in a buffer containing 6×SSC, 5 mM EDTA pH 8, 5×Denhardt, 0.1% SDS and 0.1 mg/ml ssDNA, for 2 hrs at 42° C., the membrane was hybridized overnight at 42° C. in the same buffer containing 50 ng of the CB2 oligonucleotide probe 5'-GACCCTAGGGCTAGT-GTTGGCTG-3' (SEQ ID NO:5), labeled with [γ-$^{32}$P] adenosine triphosphate, using T4 kinase (Invitrogen). After hybridization, the blot was washed twice in 0.1% SDS, 1×SSC for 30 min at room temperature and analyzed by phospho-imager (Molecular Dynamics, France).

Immunocytochemical detection of CB2 receptor in human hepatic myofibroblasts. Human hepatic myofibroblasts were seeded (1000/cm$^2$) in 35 mm dishes, grown in serum-containing medium for 24 hrs. Afterwards, immunocytochemistry was performed on cells made quiescent by a 48 hrs incubation in serum-free Waymouth medium. Briefly, cells washed with TBS and fixed in 4% paraformaldehyde for 10 min, after which they were washed in TBS and subsequently incubated in TBS/20% AB-human serum for 30 min at room temperature. Cells were then incubated with the anti-CB2 antisera (dilution 1/400 in TBS/20% AB-human serum) for 3 hrs at room temperature and overnight at 4° C. in a humid chamber. After incubation with the primary antibody, cells were rinsed extensively in TBS and incubated with a Cy3-conjugated goat anti-rabbit IgG (Sigma) (dilution 1/500, in TBS/20% AB-human serum) at room temperature, in the dark, for 30 min. Cells were then rinsed extensively in TBS, mounted in Vectashield mounting medium (Vector Laboratories, Burlingame, Calif.), sealed and observed by fluorescence microscopy. To confirm the specificity of the primary antibody, controls included preadsorption with the corresponding synthetic peptide (100 µg/ml, for 1 hr at room temperature) or omission of the primary antibody.

[$^{35}$S] GTPγS binding assay. Membranes were obtained from confluent hepatic myofibroblasts or from CHO cells overexpressing CB2 receptors (kindly provided by Sanofi, Montpellier, France) made quiescent by incubation in Waymouth medium without serum for 48 hrs, as described in [9], and frozen at −80° C. until use. [$^{35}$S] GTPγS binding was performed in the conditions described in [9]. Specific binding was calculated as the difference in bound radioactivity in the presence or absence of 10 µM unlabeled GTPγS, and did not exceed 10% of the total binding.

Apoptosis assays. All the following techniques for measuring apoptosis were performed on non-confluent cells allowed to attach overnight in DMEM 5/5 and serum-starved for 48 hrs, as previously reported [10; 11]. Nuclear morphology was assayed using DAPI staining. Cells (10,000/cm$^2$) in Lab-Tek chamber slides (Nalge Nunc International) were treated with the indicated effectors for 8 hrs, fixed in 2% paraformaldehyde, stained with DAPI and viewed under fluorescence microscopy (ZEISS). Caspase-3-like activity was assayed on cell lysates obtained as follows. After treatment of cells (200,000 cells in 60 mm dishes) for various periods of time with the indicated effectors, floating cells were collected, centrifuged and the pellet lysed in 50 μl lysis buffer containing 50 mM HEPES pH 7.4, 100 mM NaCl, 1% NP-40, 1 mM EDTA (pH 8.0), 1 mM DTT, Leupeptin 2 μg/ml, Aprotinin 2 μg/ml and pepstatin 1 μg/ml. Adherent cells were lysed for 10 min on ice, in 0.2 ml lysis buffer. The lysates from adherent and floating cells were pooled, centrifuged and the supernatant stored at −80° C. until use. DEVDase activity was measured in 200 μl assay buffer, containing 100 mM HEPES pH 7.4, 10% sucrose, 10 mM DTT, 500 μM EDTA, 50 μg protein and 20 μM AC-DEVD-AFC as fluorogenic substrate. After 3 hrs at 37° C., the fluorescence of the reaction mixture was determined with a spectrofluorometer (FL600 Microplate Fluorescence Reader (BIO-TEK, France), with excitation and emission wavelengths of 400 nm and 530 nm, respectively. DNA laddering was assayed by agarose gel electrophoresis of total DNA extracted from cells (500,000 cells in 3 dishes of 100 mm) treated for 20 hrs with the indicated effectors. Total DNA was extracted, using the Apoptotic DNA Ladder Kit according to the manufacturer's instructions, and was further incubated with 20 μg/ml RNase (DNase free) for 20 min at room temperature. Two μg of DNA was electrophoresed on a 2% agarose gel stained with SYBR Green I, and analyzed by phospho-imager (Molecular Dynamics, France).

Fluorescent measurement of intracellular reactive oxygen species. The fluorescent probe DCFH-DA (dissolved at 5 mM in absolute ethanol) was used for the assessment of intracellular reactive oxygen species (ROS). DCF fluorescence was measured using a FL-600 multiplate fluorimeter (Biotek Instruments, France), as previously described [1,1]. Cells (7,000 cells in 96-well plates) were allowed to attach overnight in DMEM 5/5, and serum-starved for 2 days in DMEM without phenol red. Cells were then loaded for 20 min at 37° C. with 5 μM of DCFH-DA in PBS and THC. After two washes in PBS, the fluorescence was monitored using excitation and emission wavelengths of 485 and 530 nm, respectively. Values were corrected for hMF autofluorescence.

Cell viability. Cells (7,000 cells in 96-well plates) were allowed to attach overnight in DMEM5/5, serum-starved for 48 hrs in DMEM without phenol red and treated with the indicated effectors for 16 hrs. CellTiter 96 AQ$_{ueous}$ One Solution reagent was added to each well and absorbance was recorded at 490 nm.

DNA synthesis. DNA synthesis was measured in triplicate wells by incorporation of [$^3$H] thymidine, as previously described [12]. Confluent hMF were made quiescent by incubation in Waymouth medium without serum for 48 hrs. Cells were then stimulated for 30 hrs with 20 ng/ml PDGF-BB. [$^3$H] thymidine (0.5 μCi/well) was added during the last 20 hrs of incubation.

Statistics. Results are expressed as mean±S.E.M of n experiments. Results were analyzed by repeated measures two-way analysis of variance (ANOVA) followed by paired comparison corrected according to the Bonferroni method. $p<0.05$ was taken as the minimum level of significance.

II. Results

CB2 Receptors are Induced in Myofibroblastic Cells of Human Cirrhotic Liver

CB2 receptor expression was studied by immunohistochemistry with a polyclonal antibody directed against human CB2 receptor, on frozen tissue sections prepared from surgical samples of normal (n=3) and cirrhotic livers (n=10) (FIGS. 1A-1C). CB2 receptors were not detected in normal liver (FIG. 1A). In contrast, cirrhotic samples showed a strong CB2 immunostaining of numerous spindle-shaped cells in fibrotic septa, irrespective of the etiology of cirrhosis (FIG. 1B). CB2 receptor expression was also found in non-parenchymal cells, as well as in inflammatory cells and bile duct epithelial cells located along fibrotic septa. Specificity of the antibody was demonstrated by the lack of signal in slides incubated in the presence of the CB2 blocking peptide (FIG. 1B, inset) or by omitting the first antibody (not shown).

Figure 2:
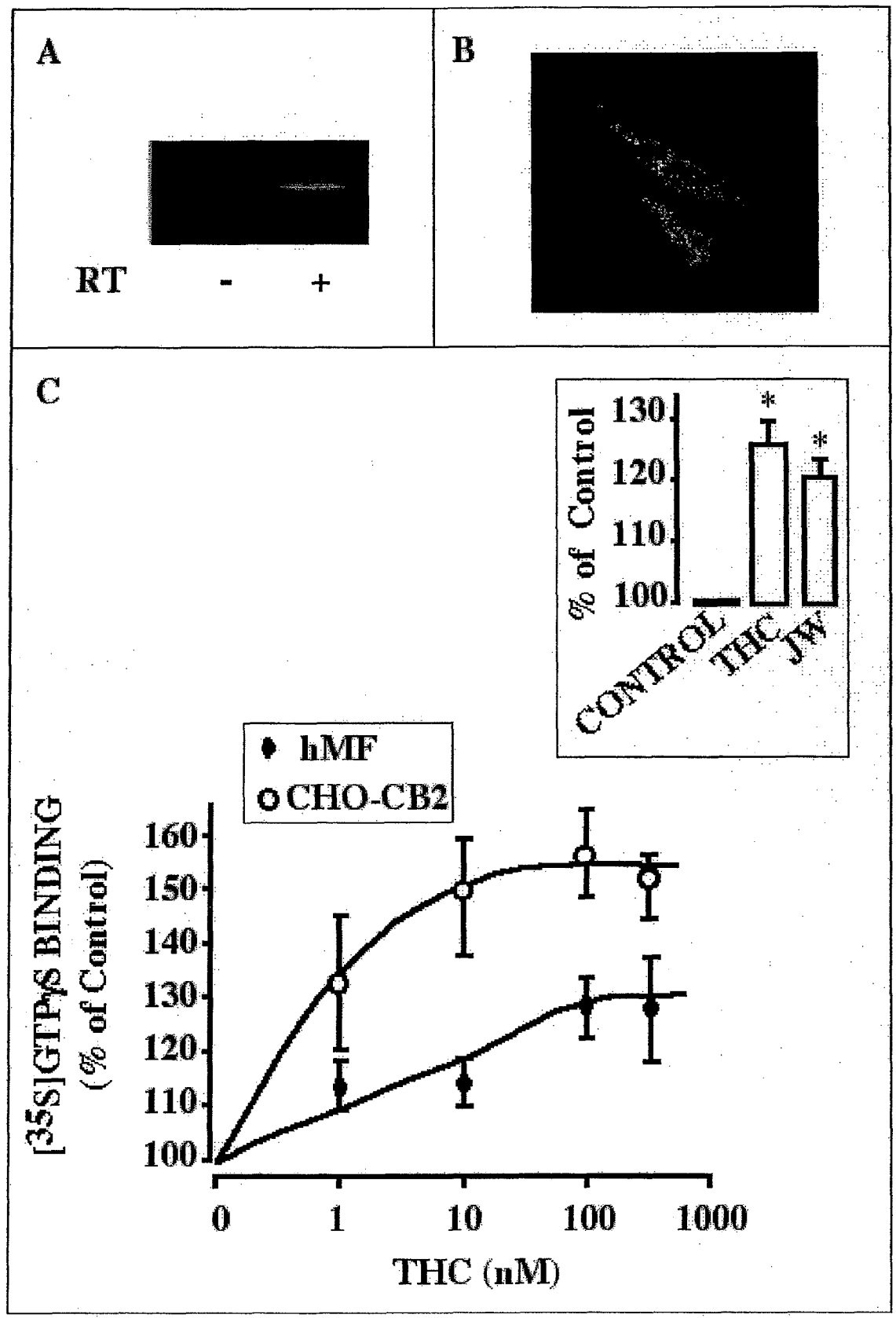
FIG. 2: CB2 receptors are expressed and functional in cultured human hepatic myofibroblasts. (A) Expression of CB2 receptor mRNA. RT-PCR for CB2 receptors was performed as described under "Methods". The PCR products were then size-fractionated, blotted and the membranes were hybridized with a labeled oligonucleotide complementary to the CB2 receptor sequences within the cDNA flanked by the PCR primers. Bands with 223 bp corresponding to the size of the CB2 receptor product was identified. (B) Expression of CB2 receptor protein. CB2 receptor protein was detected by immunofluorescence as described under "Methods" (Magnification ×630). (C) THC and JWH-015 enhance GTPγS binding in human hepatic myofibroblasts and CHO-CB2 cells. Membranes from human hepatic myofibroblasts or CHO-CB2 were assayed for [$^{35}$S]GTPγS binding assays as described under 'Methods' with varying concentrations of THC. Results represent the mean±S.E.M of seven to nine experiments and are expressed as percent of control. Inset shows stimulation of [$^{35}$S]GTPγS binding by 300 nM of THC or JWH-015 in human hepatic myofibroblasts. $P<0.001$ by 2-way ANOVA for agonists treatments.

Double immunohistochemistry, using and anti-CB2 receptor antibody and an alpha-smooth muscle actin antibody, clearly identified hepatic myofibroblasts within fibrotic septa as a major cell type expressing CB2 receptors (FIG. 1C). Accordingly, CB2 receptors were also expressed in cultured human hepatic myofibroblasts, as demonstrated both by RT-PCR analysis (FIG. 2A) and by immunocytochemistry (FIG. 2B).

The functionality of CB2 receptors expressed in human hepatic myofibroblasts was studied in [$^{35}$S] GTPγS binding assays, which measure GDP-GTP exchange on the a (alpha) subunit of the G protein, and reflect the initial steps of G protein activation by a receptor ligand. CHO cells overexpressing CB2 receptors served as controls. As shown in FIG. 2C, Δ9-tetrahydrocannabinol (THC), a natural cannabinoid that binds to both CB1 and CB2 receptors, dose-dependently increased binding of [$^{35}$S] GTPγS to G proteins in membranes of human hepatic myofibroblasts, with an EC50 of 10 nM and a maximal effect observed at 100 nM. In CHO-CB2 overexpressing cells, the EC50 was 1 nM, and maximal activation occurred at 10 nM (FIG. 2C). The specific CB2 agonist JWH-015, which selectively binds to CB2 receptors with a potency similar to that of THC, was as efficient as THC in enhancing GTPγS binding (FIG. 2C, inset).

Antiproliferative Effect of CB2 Receptors in Human Hepatic Myofibroblasts

THC dose-dependently inhibited DNA synthesis elicited by 20 ng/ml PDGF-BB (FIG. 3A), with a maximal 50% reduction of growth at 500 nM THC, half maximal inhibition occurring in the presence of 200 nM of the compound.

Figure 3:
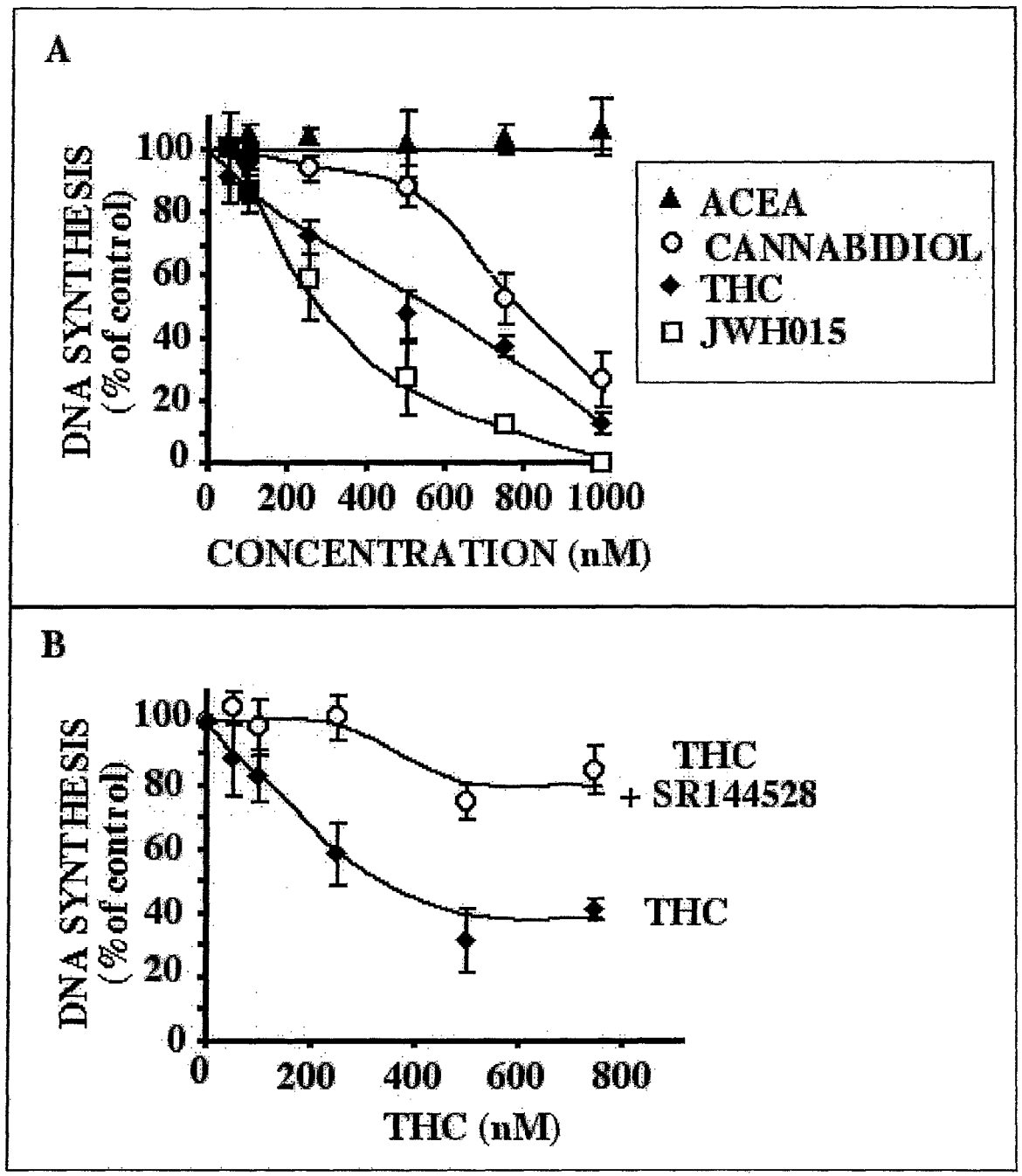
FIG. 3: Cannabinoids inhibit DNA synthesis in human hepatic myofibroblasts via a CB2 receptor-dependent pathway. (A) Effects of cannabinoids on DNA synthesis. Confluent human hepatic myofibroblasts were made quiescent by incubation in serum-free medium over 3 days. Cells were stimulated for 30 hrs with varying concentrations of THC, JWH-015, cannabidiol and ACEA, in the presence of 20 ng/ml of PDGF (platelet-derived growth factor). [$^{3}$H]Thymidine incorporation into DNA was measured as described under "Methods". Results represent the mean±SEM of 3 to 6 experiments and are expressed as percent of control. $p<0.05$ compared to control. Inset: Effects of selective CB1 and CB2 receptor agonists on cAMP production in CHO cells overexpressing CB1 or CB2 receptor. Confluent quiescent CHO cells overexpressing CB1 or CB2 receptors were exposed for 10 min to 100 nM of JWH015, ACEA and cannabidiol or the respective concentrations of vehicle (ethanol for ACEA and JWH015, methanol for cannabidiol). Cyclic AMP was extracted and measured as described under "Methods". (B) Inhibition of DNA synthesis by THC is blocked by a CB2 receptor antagonist. Confluent quiescent cells were pretreated for 1 hr with 1 μM of the CB2 receptor antagonist SR144528 or vehicle. DNA synthesis was then measured as described in (A). Results represent the mean±SEM of 6 experiments. $p<0.05$ for THC vs vehicle and for THC+SR144528 vs THC.

We further defined the receptor involved, owing to the use of selective CB2 agonists (JWH-015 and cannabidiol) and of a selective CB1 agonist (ACEA). Specificity of the compounds for their respective receptors was verified by assessing their effects in CHO cells overexpressing CB1 or CB2 receptors. In CHO overexpressing CB2 receptors, JW-015 strongly decreased forskolin-stimulated cAMP levels, while ACEA had no effect; conversely, in CHO overexpressing CB1 receptors, ACEA reduced forskolin-stimulated cAMP levels, whereas JW-015 had no effect (FIG. 3A, inset). In human hepatic myofibroblasts, the selective CB2 receptor agonist JWH-015 was as potent as THC in inhibiting DNA synthesis (IC50 150 nM), inducing a maximal 60% reduction of PDGF-BB-stimulated DNA synthesis at 500 nM. In contrast, the CB1 agonist ACEA had no effect (FIG. 3A). In keeping with these results, pretreatment of cells with the CB2 receptor antagonist SR 144528 strongly reduced the antiproliferative effect of THC (FIG. 3B). These results demonstrate that the growth inhibitory effects of THC rely on CB2 receptor activation.

Activation of CB2 Receptors Induce Apoptosis of Human Hepatic Myofibroblasts

Figure 4:
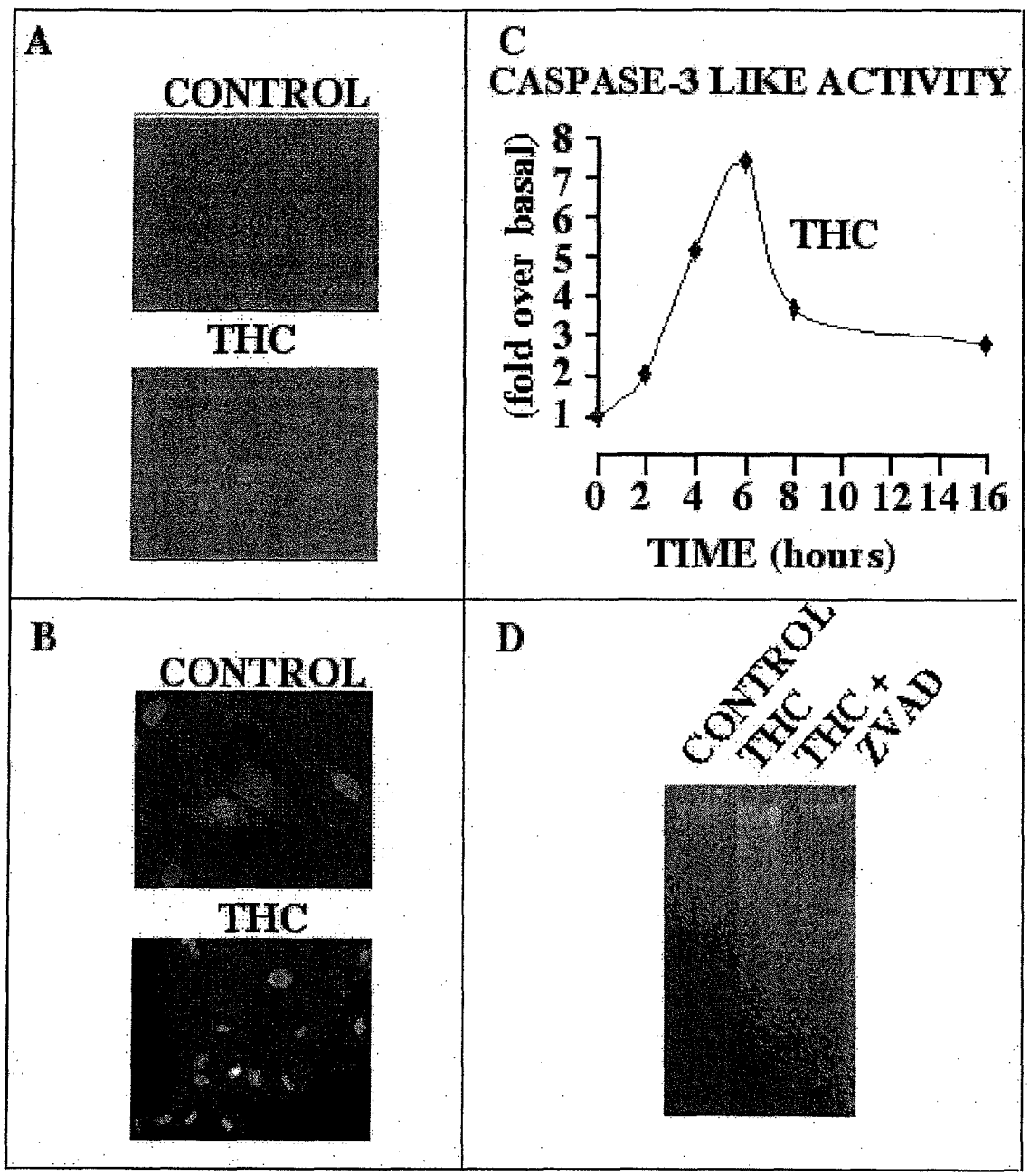
FIG. 4: Cannabinoids trigger human hepatic myofibroblast death by an apoptotic mechanism. (A) Phase-contrast analysis (Magnification ×100). Serum-deprived cells were incubated for 16 h with 4 μm THC or vehicle. (B) DAPI staining of the nuclei (Magnification ×630) Serum-deprived cells were incubated for 16 h with 4 μm THC or vehicle. (C) Caspase-3-like activity. Caspase-3-like activity kinetic was assayed on cell lysates at the indicated time point as described under "Methods." (D) DNA ladder formation. DNA was extracted and analyzed by electrophoresis on a 2% agarose gel stained with SYBR Green I. Serum-deprived cells were preincubated for 1 h with 50 μM ZVAD or vehicle and further incubated for 16 h in the presence of 50 μM ZVAD or vehicle, together with either 4 μM of THC or vehicle.

THC also elicited cytotoxic effects towards serum-deprived human hepatic myofibroblasts, as shown by cell rounding, shrinkage and detachment (FIG. 4A). Maximal decrease in cell survival was observed at 2 μM THC, a concentration higher than that required to trigger growth inhibition. Several lines of evidence indicated that reduced viability was related to an apoptotic process. DAPI staining showed that cells exposed to THC exhibited condensed nuclei in contrast to control cells (FIG. 4B). Consistently, THC induced a time-dependent activation of caspase-3, with a maximal 6.7-fold±1.3 increase in activity peaking after 4-6 hr (FIG. 4C); as expected, the general caspase inhibitor ZVAD-fmk totally blunted caspase-3 stimulation by THC (not shown). Finally, THC-treated cells showed dramatic DNA laddering on agarose gel electrophoresis, in contrast to control serum-deprived cells which displayed intact DNA (FIG. 4D). ZVAD-fmk also blocked THC-induced DNA laddering (FIG. 4D).

Figure 5:
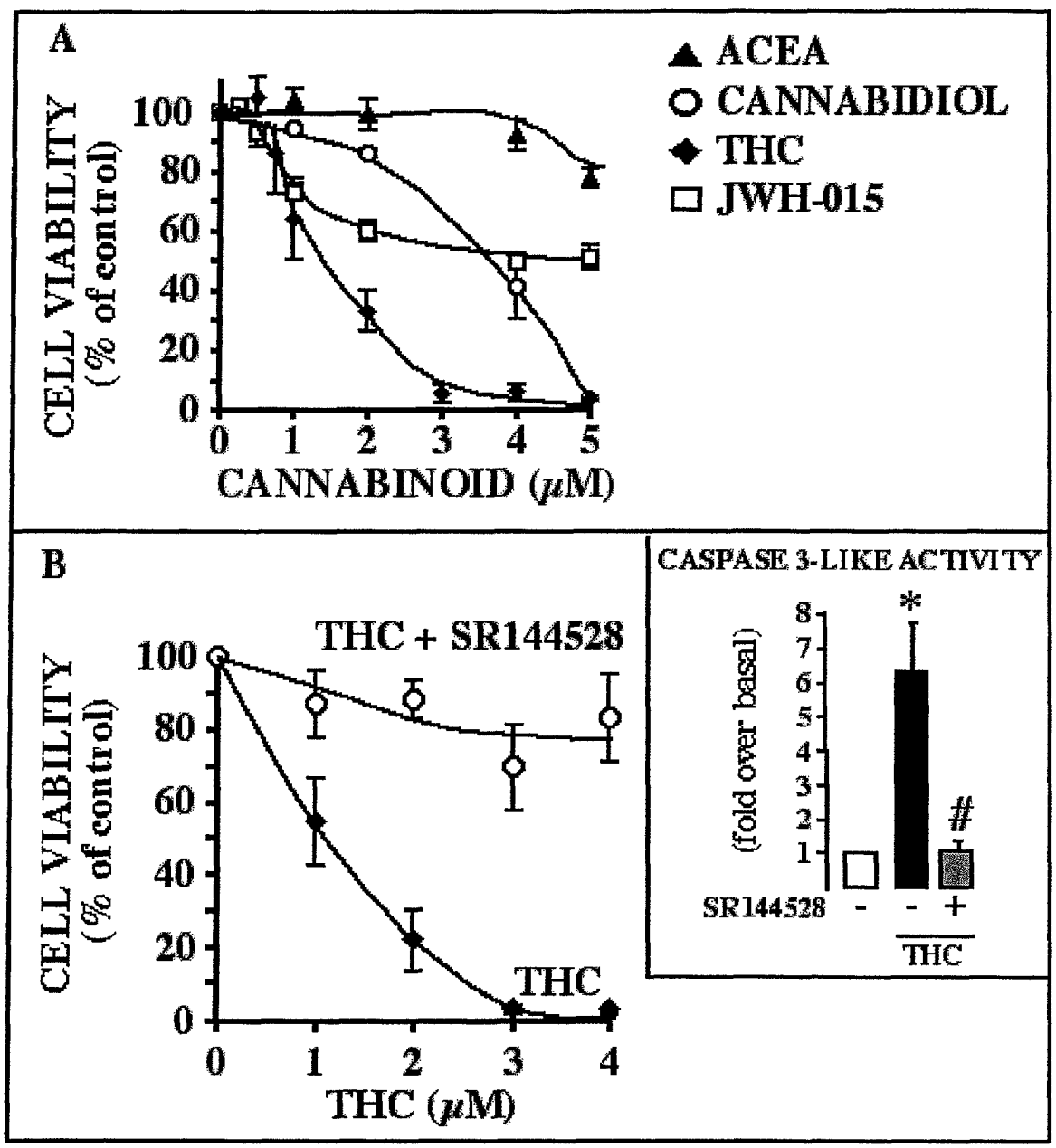
FIG. 5: Cannabinoids triggers apoptosis via a CB2 receptor-dependent pathway. (A) Effects of THC and CB1 and CB2 receptor selective agonists on hepatic myofibroblast viability. Serum-deprived cells were incubated with varying concentrations of THC, JWH015, cannabidiol and ACEA for 16 hours. Cell viability was determined as described under "Experimental procedures". Results are the mean+/−S.E.M. of 3 to 6 experiments ($p<0.05$ compared with vehicle). (B) Apoptosis triggered by THC is blocked by a CB2 receptor antagonist. Serum-deprived cells were preincubated for 1 h with 2 μM of SR144528 or vehicle, and further incubated with varying concentrations of THC for 16 hours. Cell viability was determined as described under "Experimental procedures". Results are the mean+/−S.E.M. of 6 experiments ($p<0.05$ for THC vs vehicle and for THC+SR144528 vs THC). Inset: Effects of SR144528 on caspase-3 activation by THC. Serum-deprived cells were preincubated for 1 h with 2 μM of SR144528 or vehicle, and further incubated with 4 μM of THC or vehicle for 5 hours. Caspase-3-like activity was assayed on lysates, as described under "Methods". Results are the mean+/−S.E.M of 5 experiments ($p<0.05$ for THC vs vehicle and for THC+SR144528 vs THC). SR144528 alone had no effect either on cell viability or caspase-3 like activity.

Further experiments investigated whether THC-induced apoptosis was receptor-mediated. THC elicited a dose-dependent decrease in cell viability, as assessed by the MTS assay, half maximal inhibition occurring with a 1.5 µM concentration of the compound (FIG. 5A). JWH-015 also dose-dependently reduced hepatic myofibroblast viability, half maximal effect occurring at 1 µM concentrations of the compound (FIG. 5A). The cytotoxic effect of THC was blunted in cells pretreated with the selective CB2 receptor antagonist SR 144528 (FIG. 6B), and accordingly, cells exposed to SR 144528 showed no activation of caspase-3 in response to THC (FIG. 5, inset).

Molecular Mechanisms Mediating THC-Induced Growth Inhibition and Apoptosis.

Figure 6:
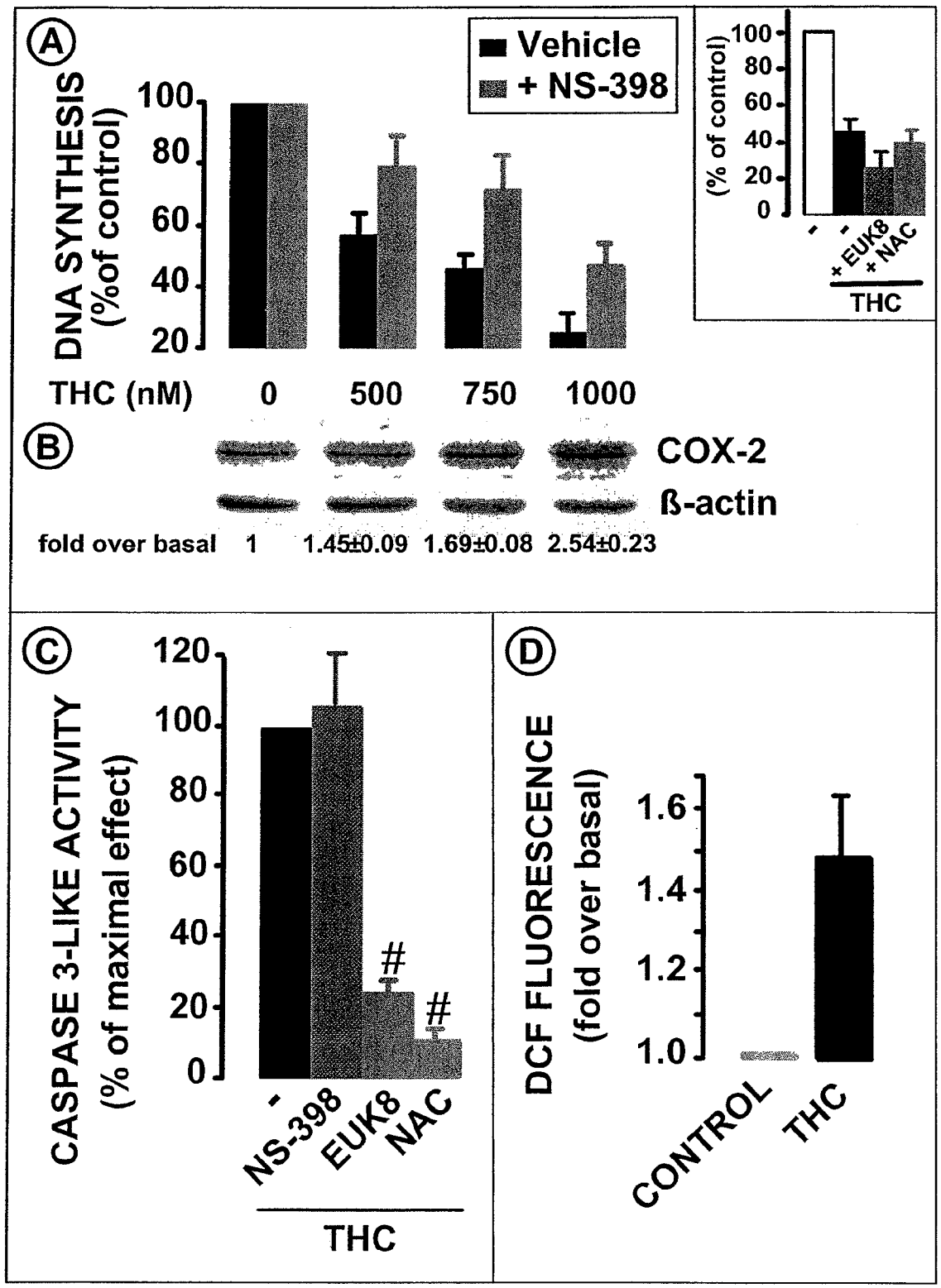
FIG. 6: Growth inhibitory and apoptotic effects of THC are mediated by two distinct signaling pathways. (A) COX-2 mediates inhibition of human hepatic myofibroblast proliferation by THC. Cells were pretreated for 1 h with 10 μM NS-398 or vehicle, further stimulated with 20 ng/ml PDGF-BB and varying concentrations of THC, and DNA synthesis was measured as in FIG. 3. Results (mean±SEM, n=3-5) are expressed as percent of respective control (17000±6000 cpm for PDGF-BB; 34000±12000 cpm for PDGF-BB+NS-398). $p<0.05$ for NS-398 effects. Inset: Cells were pretreated for 1 h with 5 mM NAC, 25 μM EUK8 or vehicle and further stimulated 20 ng/ml PDGF-BB and 750 nM THC. (B) THC induces COX-2 and stimulates COX activity in human hepatic myofibroblasts. Western blot analysis of COX-2 protein induction in extracts of cells treated with varying concentrations of THC for 8 h (n=3). A typical blot is shown. Results were normalized relative to β-actin expression. COX activity was assayed after 8 h incubation with 1000 nM THC. At the end of incubation, 10 μM of arachidonic acid was added for 30 min and PGE2 released in the supernatants was measured as described under "Methods". Results are the mean of sextuplet determinations obtained from 2 experiments (# $p<0.05$ vs control).s. (C) THC-induced apoptosis involves ROS production. Serum-deprived hepatic myofibroblasts were pretreated for 1 hr with either 5 mM NAC (N-Acetyl Cysteine), 110 M EUK8 or vehicle. Caspase 3-like activity was assayed as in FIG. 4, after a 5 hr treatment with 4 μM THC or vehicle (mean±SEM, n=3; # $p<0.05$ vs THC). Antioxidants added alone had no effect on caspase-3-like activity. Maximal increase of caspase-3 activity by THC was 6.3±2 fold (100%). (D) Effect of THC on the production of reactive oxygen species (ROS). Human hepatic myofibroblasts were loaded with DCFH-DA (dichlorofluoroscein diacetate) for 20 min at 37° C., together with 3 μM THC and the fluorescence was monitored in a FL-600 fluorimeter. Results are the mean+/−SEM of 6 experiments. # $P<0.05$ for THC vs basal.

We investigated the molecular mechanism of THC-induced growth inhibition of human hepatic myofibroblasts and focused on the inducible form of cyclooxygenase, cyclooxygenase-2 (COX-2), since we previously showed that COX-2 induction is a major antiproliferative pathway in human hepatic myofibroblasts [13; 14; 9]. We investigated whether COX-2 might also be involved in cannabinoid elicited growth inhibition, owing to the use of NS-398, a selective COX-2 inhibitor. As shown in FIG. 6A, NS-398 reduced the antiproliferative effect of THC. Accordingly, THC caused a strong induction of COX-2, (FIG. 6B). In contrast ibuprofen or NS-398 did not affect THC-induced caspase-3 (FIG. 6c).

We recently unraveled oxidative stress as a mediator of apoptosis elicited by 15-d-prostaglandin J2 [11]. Therefore, subsequent experiments were designed in order to investigate whether CB2-dependent apoptosis relies on oxidative stress. Two antioxidants were used, EUK 8, a superoxide dismutase and catalase mimetic with potent antioxidant effects, and the glutathione precursor N-Acetyl Cysteine (NAC). Both compounds blunted activation of caspase-3 elicited by THC (FIG. 6C). Accordingly, treatment of cells with 3 µM THC increased by 1.5 fold the production of intracellular reactive oxygen species, as assessed with the peroxide-sensitive probe DFCH-DA. (FIG. 6D). In contrast, EUK 8 or NAC did not affect THC-induced growth inhibition (FIG. 6A).

Taken together, these results demonstrate that growth inhibitory and apoptotic effects of CB2 receptors depends on distinct signalling pathways, induction of COX-2 and intracellular oxidative stress, respectively.

III. Discussion

Proliferation of myofibroblasts is central for the development of liver fibrosis during chronic liver diseases. We provide here the first evidence that CB2 receptors are induced in hepatic myofibroblasts of patients with cirrhosis of various etiologies. Moreover, our results demonstrate that activation of CB2 receptors reduce accumulation of human hepatic myofibroblasts by eliciting growth inhibitory and apoptotic effects.

Data concerning expression and function of CB receptors in liver are scarce. It was previously shown that normal liver does not express CB2 receptor mRNA. Accordingly, we did not detect CB2 by immunohistochemistry in normal human liver samples. In contrast, we show that CB2 receptors are strongly induced in the cirrhotic liver of various etiologies and are expressed in non parenchymal cells and biliary cells located within and at the edges of fibrotic septa. Double immunohistochemistry identified hepatic myofibroblasts as a major cell type expressing CB2 receptors during chronic liver diseases. Heterogeneity of liver fibrogenic cells has recently been documented, with the description of at least two populations of smooth muscle α-actin myofibroblasts with fibrogenic potential, myofibroblastic hepatic stellate cells and hepatic myofibroblasts, both of which accumulate during chronic liver injury (15, 16). Our experiments were performed with cultured hepatic myofibroblasts (smooth muscle alpha actin and fibulin-2 positive cells) and confirmed the expression of CB2 mRNA and protein in these fibrogenic cells. Moreover, GTPγS binding experiments demonstrated that CB2 receptors are functional. Indeed, THC induced activation of G protein with an affinity of 10 nM, in keeping with the apparent affinity of THC for its receptors. In addition, JWH-015, the selective CB2 agonist, also elicited G protein activation, with a potency similar to that of THC. Although CB2 receptors are predominantly expressed in spleen, tonsils and immune cells, they have also been detected at low levels in various tissues. Interestingly, the presence of CB2 receptors has also been described in mesangial cells, a cell type that contributes to the pathogenesis of renal matrix accumulation during chronic glomerular injury.

The ability of cannabinoids to control cell death and proliferation has been well documented. Thus, antitumoral properties of cannabinoids have been linked to their growth inhibitory and apoptotic effects. Indeed, activation of CB2 receptors induce apoptosis of glioma cells in culture and regression of malignant glioma in vivo. Cannabinoids also induce cell death in PC-12 pheochromocytoma cells, tumorigenic epidermal cells, and K-ras-transformed epithelial cells, via either CB1 or CB2-dependent pathways (for a review, see 17). Moreover, proliferation of breast and prostate cancer cells is strongly reduced by cannabinoids. We show herein that, in human hepatic myofibroblasts, CB2 triggers two major antifibrogenic properties of human hepatic myofibroblasts, growth inhibition and apoptosis. These effects are elicited by different cannabinoid concentrations, since sub-micromolar concentrations of THC inhibited growth without affecting cell viability, whereas apoptosis only occurred at micromolar concentrations. Such dose-dependent selectivity of antiproliferative and apoptotic effects has previously been described. Thus, in fetal hepatocytes, growth inhibition and apoptosis require different concentrations of TGF-β[18]. Similarly, low concentrations of two lipids, 15-d-PGJ2 and SIP are growth inhibitory for human hepatic myofibroblasts, whereas higher doses are apoptotic [19; 11; 9; 10]. Nevertheless, both THC-mediated growth arrest and cell death of human hepatic myofibroblasts were CB2 receptor-dependent, as shown by the use of selective CB2 agonists and antagonists. Thus, both effects were blocked by the CB2 receptor antagonist SR144528, and reproduced by the CB2 agonists cannabidiol and JW-015, but not by the CB1 agonist ACEA. In several studies, similar micromolar concentrations of cannabinoids were also required to induce receptor-mediated apoptosis, in particular in leukemia and lymphoma cells (19), or in human breast cancer cells (20). The reason as to why such concentrations of THC are required to induce cell death are undefined, but CB2 receptor dimerization could provide an explanation. Indeed, it is well established that homo- or heterodimerization of G protein-coupled receptors leads to increased or decreased potency of agonists to induce functional responses. Thus, orexin 1/CB1 receptor dimers show enhanced efficacy for orexin 1-mediated ERK activation. In contrast, neurotensin receptor 1 and 3 complexes show decreased potency of neurotensin for neurotensin receptor 1-mediated functional responses. Further investigations are warranted to determine whether CB2 receptors can form homo or heterodimers in human hepatic myofibroblasts.

Characterization of the molecular mechanisms underlying growth arrest and apoptosis following CB2 activation revealed distinct, non overlapping signalling pathways. Antiproliferative effects of THC rely on COX-2 induction and apoptosis is mediated by oxidative stress. In human breast cancer cells, the growth inhibitory effect of anandamide was consecutive to inhibition of cyclic AMP (cAMP) levels. However, this mechanism is unlikely in human hepatic myofibroblasts, since we have shown that cAMP is an antiproliferative messenger [13; 14; 9], and cAMP levels are not raised in response to THC in human hepatic myofibroblasts (not shown). We show that, in human hepatic myofibroblasts, growth inhibition by cannabinoids is tightly controlled by cyclooxygenases, the rate-limiting enzymes in the conversion of arachidonic acid into prostaglandins and thromboxanes. We previously showed that COX-2, the inducible form of cyclooxygenase, is central in growth inhibition of human hepatic myofibroblasts. We described that endothelin-1, TNF-α and sphingosine-1-phosphate inhibit proliferation of these cells through a pathway that involves induction of COX-2. We also showed that the mitogenic effects of PDGF-BB and thrombin result from a balance between a promitogenic and a COX-2-dependent growth inhibitory pathway. Although a few studies suggested that cannabinoids stimulate arachidonic acid release in cultured astrocytes and neuroblastoma cells, and increase PGE2 production in the brain, induction of COX-2 by cannabinoids was described only in neuroglioma cells and lung cancer cells (39, 40). However, these studies did not investigate the biological consequences of the production of arachidonic metabolites. We show here that NS-398, a selective COX-2 inhibitor, reduces the growth inhibitory effect of THC, demonstrating that the antiproliferative effects of cannabinoids rely on COX-2 induction. Accordingly, THC triggers induction of COX-2. Therefore, the present data further support a central role of COX-2 in human hepatic myofibroblast growth inhibition, although additional mechanisms may be involved. The consequences of COX-2 induction by THC may involve regulation of more distal events, such as cell cycle components.

We also demonstrate that apoptosis elicited by THC relies on an intracellular pathway distinct from that involved in growth inhibition. Indeed, blocking COX-2 by NS398 did not affect cell death triggered by THC, suggesting the involvement of other signaling pathways. In contrast, the antioxidants NAC and EUK 8, a superoxide/catalase mimetic decrease the apoptotic response to THC (FIG. 7) without affecting growth inhibition elicited by the compound. These results indicate that THC-dependent apoptosis is mediated by oxidative stress, a result further supported by the finding that apoptotic doses of THC also stimulates ROS production (FIG. 7). Production of ROS occurs rapidly, being observed within 20 min exposure to THC, and therefore appears as an early signaling event in the apoptotic signaling pathway. Increasing evidences suggest a major role for ROS as intermediates for apoptosis signaling. Thus, production of ROS leads to growth inhibition and apoptosis of tumor and hematopoietic cells, in response to HGF, TNF-α, or Fas ligand. The signaling events initiated by ROS following THC stimulation and leading to human hepatic myofibroblast apoptosis are under current investigation. Ceramide might be a possible candidate, since it triggers apoptosis in human hepatic myofibroblasts, and is associated with apoptosis in response to cannabinoids in different cell types.

Accumulation of hMF is one of the hallmarks of the fibrogenic process in the liver and several lines of evidence indicate that limiting proliferation of these cells or inducing their apoptosis may represent promising therapeutic approaches. Along these lines, it was recently demonstrated in a model of chronic tetrachloride intoxication that withdrawal of the insulting agent is followed by apoptotic removal of hMF and resolution of fibrosis. The causal link between hMF apoptosis and reversibility of fibrosis was further reinforced in a study demonstrating that administration of gliotoxin induces apoptosis of activated MF in vitro and in vivo, reduces progression of fibrosis during tetrachloride intoxication and enhances regression of fibrosis during the recovery phase. The balance between pro and anti-apoptotic factors for hMF may therefore be critical in the progression of liver fibrosis. This was recently exemplified with TIMP-1, a strong survival factor for activated MF, as shown by the fact that prolonged expression of TIMP-1 is associated to a decreased spontaneous resolution of liver fibrosis. We show that CB2 receptors are not detected in the normal liver and are strongly induced in hepatic myofibroblasts in the cirrhotic liver. These results indicate that activation of CB2 receptors during chronic liver disease can limit progression of fibrosis. Interestingly, there appears to be a general up-regulation of the cannabinoid system during chronic liver diseases. Indeed, it was recently shown that there is an increased production of endogenous anandamide by monocytes of patients with chronic liver diseases which is associated to up-regulation of CB1 receptors in vascular endothelial cells. These alterations elicit an increase in peripheral vasodilation and contribute to the pathogenesis of portal hypertension through activation of CB1 receptors.

To briefly summarize, immunohistochemistry experiments indicated that, in the normal liver, CB1 receptors were expressed around vessels, whereas CB2 receptors were not or faintly detected. However, human hepatic myofibroblasts express the receptors for cannabinoids CB1 and CB2. In biopsies from patients with chronic liver diseases, CB1 and CB2 receptors were detected in non parenchymal cells, in the lobule and in the fibrous septa. CB1 and CB2 receptor mRNAs and proteins were also detected in cultured human hepatic myofibroblasts, as detected by RT-PCR and immunocytochemistry. Δ9-tetrahydrocannabinol, the main active component of marijuana, reduced viability of serum-deprived hepatic myofibroblasts by an apoptotic process, characterized by condensed nuclei, fragmented DNA and increased caspase-3 activity.

Apoptosis involved CB receptors since the CB1/CB2 agonists CP 55940, HU-210, WIN-55.212-2, as well as anandamide were also cytotoxic. Apoptosis was triggered by CB2 receptors since i) the CB1 agonist ACEA was not cytotoxic, whereas the CB2 agonist JWH-015 was apoptotic, and ii) the CB2 antagonist SR 144528 prevented apoptosis elicited by HU-210, whereas the CB1 antagonist SR 141716 had no effect.

In conclusion, activation of CB2 leads to potent apoptosis of human hepatic myofibroblasts and may therefore limit their accumulation during liver fibrosis. The data presented herein show CB2 receptors as a novel antifibrogenic pathway in hMF. This pathway is up-regulated in cirrhotic patients, indicating that a CB2-based antifibrotic strategy can be used, which is devoid of non desired CB1-mediated psychotropic and vasodilating effects.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

REFERENCES

1. Friedman, S. L. (2000) J Biol Chem 275, 2247-2250
2. Piomelli, D., Giuffrida, A., Calignano, A., and Rodriguez de Fonseca, F. (2000) Trends Pharmacol Sci 21, 218-224.
3. Kumar, R. N., Chambers, W. A., and Pertwee, R. G. (2001) Anaesthesia 56, 1059-1068.
4. Bifulco, M., Laezza, C., Portella, G., Vitale, M., Orlando, P., De Petrocellis, L., and Di Marzo, V. (2001) Faseb J 29, 29
5. Pertwee, R. G. (1999) Curr Med Chem 6, 635-664.
6. Guzman, M., and Sanchez, C. (1999) Life Sci 65, 657-664
7. Batkai, S., Jarai, Z., Wagner, J. A., Goparaju, S. K., Varga, K., Liu, J., Wang, L., Mirshahi, F., Khanolkar, A. D., Makriyannis, A., Urbaschek, R., Garcia, N., Jr., Sanyal, A. J., and Kunos, G. (2001) Nat Med 7, 827-832
8. Rinaldi-Carmona, M., Barth, F., Millan, J., Derocq, J. M., Casellas, P., Congy, C., Oustric, D., Sarran, M., Bouaboula, M., Calandra, B., Portier, M., Shire, D., Breliere, J. C., and Le Fur, G. L. (1998) J Pharmacol Exp Ther 284, 644-650
9. Davaille, J., Gallois, C., Habib, A., Li, L., Mallat, A., Tao, J., Levade, T., and Lotersztajn, S. (2000) J Biol Chem 275, 34628-34633
10. Davaille, J., Li, L., Mallat, A., and Lotersztajn, S. (2002) J Biol Chem 277, 37323-37330.
11. Li, L., Tao, J., Davaille, J., Feral, C., Mallat, A., Rieusset, J., Vidal, H., and Lotersztajn, S. (2001) J Biol Chem 276, 38152-38158.
12. Tao, J., Mallat, A., Gallois, C., Belmadani, S., Méry, P. F., Nhieu, J. T., Pavoine, C., and Lotersztajn, S. (1999) J Biol Chem 274, 23761-23769
13. Mallat, A., Gallois, C., Tao, J., Habib, A., Maclouf, J., Mavier, P., Preaux, A. M., and Lotersztajn, S. (1998) J Biol Chem 273, 27300-27305
14. Mallat, A., Fouassier, L., Preaux, A. M., Gal, C. S., Raufaste, D., Rosenbaum, J., Dhumeaux, D., Jouneaux, C., Mavier, P., and Lotersztajn, S. (1995) J Clin Invest 96, 42-49
15. Knittel, T., Kobold, D., Saile, B., Grundmann, A., Neubauer, K., Piscaglia, F., and Ramadori, G. (1999) Gastroenterology 117, 1205-1221
16. Cassiman, D., and Roskams, T. (2002) J Hepatol 37, 527
17. Guzman, M., Sanchez, C., and Galve-Roperh, I. (2001) J Mol Med 78, 613-625
18. Sanchez, A., Alvarez, A. M., Benito, M., and Fabregat, I. (1996) J Biol Chem 271, 7416-7422
19. McKallip, R. J., Lombard, C., Fisher, M., Martin, B. R., Ryu, S., Grant, S., Nagarkatti, P. S., and Nagarkatti, M. (2002) Blood 100, 627-634
20. De Petrocellis, L., Melck, D., Palmisano, A., Bisogno, T., Laezza, C., Bifulco, M., and Di Marzo, V. (1998) Proc Natl Acad Sci USA 95, 8375-8380
21. Ramer, R., Brune, K., Pahl, A., and Hinz, B. (2001) Biochem Biophys Res Commun 286, 1144-1152
22. Gardner, B., Zhu, L. X., Sharma, S., Tashkin, D. P., and Dubinett, S. M. (2003) Faseb J 17, 2157-2159.
23. Mechoulam et al. (1995) Biochem. Pharmacol. 50:83.

What is claimed is:

1. A method of treating a disease of the liver, comprising administering an effective amount of a cannabinoid to a patient having the disease, wherein the disease is liver fibrosis.

2. A method of treating a disease of the liver, comprising administering an agent that activates a CB2 receptor to a patient having the disease, wherein the disease is liver fibrosis.

3. A method of treating a disease of the liver, comprising administering a composition comprising a non-selective agonist of CB2 and a selective antagonist of CB1 to a patient having the disease, wherein the disease is liver fibrosis.

4. A method of treating a disease of the liver, comprising administering a composition comprising an agonist of CB2 receptors to a patient having the disease, wherein the disease is liver fibrosis.

5. A method of treating a disease of the liver, comprising administering a composition comprising an up-regulator of CB2 receptors to a patient having the disease, wherein the disease is liver fibrosis.

* * * * *